United States Patent
Kast et al.

[11] Patent Number: 5,559,218
[45] Date of Patent: Sep. 24, 1996

[54] 2-AROYLCYCLOHEXANEDIONES AND THEIR USE AS HERBICIDES OR PLANT GROWTH-REGULATING AGENTS

[75] Inventors: Jürgen Kast, Böhl-Iggelheim; Wolfgang von Deyn, Neustadt; Christoph Nübling, Hassloch; Helmut Walter, Obrigheim; Matthias Gerber, Limburgerhof; Karl-Otto Westphalen, Speyer, all of Germany

[73] Assignee: BASF Aktiengesellschaft, Ludwigshafen, Germany

[21] Appl. No.: 384,155

[22] Filed: Feb. 6, 1995

[30] Foreign Application Priority Data

Feb. 7, 1994 [DE] Germany .................. 44 03 670.1

[51] Int. Cl.[6] .................. C07C 245/02; C07C 317/12; C07C 321/22; A01N 41/10
[52] U.S. Cl. .................. 534/850; 504/189; 504/315; 504/333; 504/336; 558/442; 560/9; 560/11; 564/85; 564/162; 568/43; 568/44; 568/42; 568/37; 568/31
[58] Field of Search .................. 568/43, 44, 31, 568/37, 42; 534/850; 564/85, 162; 558/442; 560/9, 11; 504/189, 315, 333, 336

[56] References Cited

U.S. PATENT DOCUMENTS

| | | | |
|---|---|---|---|
| 4,909,835 | 3/1990 | Tobler | 568/43 X |
| 5,169,988 | 12/1992 | Tobler | 568/31 |
| 5,245,041 | 9/1993 | Reissenweber et al. | 568/43 X |

FOREIGN PATENT DOCUMENTS

| | | | |
|---|---|---|---|
| 2055886 | 5/1992 | Canada | 568/43 |
| 487454 | 5/1992 | European Pat. Off. | 568/43 |
| 93/16062 | 8/1993 | WIPO | 568/43 |

OTHER PUBLICATIONS

English Abstract of JP-3052862A, Jul. 20, 1989, Nippon Soda KK.
English Abstract of JP-3120202A, Oct. 3, 1989, Sandoz AG.

*Primary Examiner*—Floyd D. Higel
*Attorney, Agent, or Firm*—Keil & Weinkauf

[57] ABSTRACT

2-Aroylcyclohexanediones I

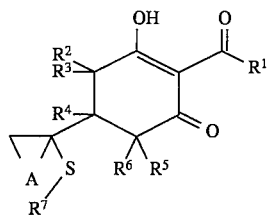

(A is $C_1$–$C_6$-alkylene; $R^1$ is substituted phenyl or hetaryl which may furthermore carry a fused ring; $R^2$–$R^5$ are each hydrogen or $C_1$–$C_4$-alkyl; $R^6$ is H, $C_1$–$C_4$-alkyl or $C_1$–$C_4$-alkoxycarbonyl and $R^7$ is $C_1$–$C_4$-alkyl, with the proviso that $R^1$ is not mono- or dihalophenyl) and the agriculturally useful salts thereof and the esters of I with $C_1$–$C_{10}$-carboxylic acids or inorganic acids.

The 2-aroylcyclohexanediones I are suitable as herbicides and plant growth regulators.

6 Claims, No Drawings

2-AROYLCYCLOHEXANEDIONES AND THEIR USE AS HERBICIDES OR PLANT GROWTH-REGULATING AGENTS

The present invention relates to novel 2-aroylcyclohexanediones of the formula I

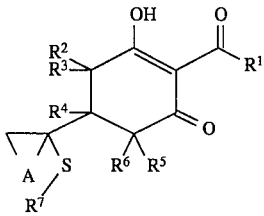

where

A is $C_1$–$C_6$-alkylene;

$R^1$ is the phenyl ring or a 5-membered or 6-membered hetaryl ring, each phenyl or hetaryl ring carrying at least one substituent but not more than four substituents, each selected from the group consisting of halogen, cyano, nitro, —N=N—Ph, —S(O)$_m$R$^8$, ($C_1$–$C_4$-alkoxy)carbonyl, —SO$_2$—N(R$^9$)R$^{10}$, —N(R$^9$)—COR$^{10}$, —N(R$^9$)—SO$_2$R$^{11}$, $C_1$–$C_4$-alkyl, $C_1$–$C_4$-alkoxy, $C_1$–$C_4$-haloalkyl and $C_1$–$C_4$-haloalkoxy, where the four last-mentioned radicals in turn may carry one or two of the following substituents: $C_1$–$C_4$-alkoxy, $C_1$–$C_4$alkylthio and/or cyano, and where two adjacent carbon atoms of the phenyl and hetaryl rings may furthermore be bridged via a chain
—C(R$^{12}$)=C(R$^{13}$)—C(R$^{14}$)=C(R$^{15}$)—,
—X—C(R$^{12}$)=N—,
—X—N=C(R$^{12}$)—, —C(R$^{12}$)=N—C(R$^{14}$,R$^{15}$)—X—,
—C(R$^{12}$)=N—C(R$^{13}$,R$^{14}$)—,
—X—C(R$^{12}$)=C(R$^{13}$)—,
—X—C(R$^{12}$)=C(R$^{13}$)—C(R$^{14}$,R$^{15}$)—, —X—C(R$^{12}$, R$^{13}$)—C(R$^{14}$,R$^{15}$)—,
—C(R$^{12}$,R$^{13}$)—X—C(R$^{14}$,R$^{15}$)—, —X—C(R$^{12}$,R$^{13}$)—Y—,
—X—C(R$^{12}$,R$^{13}$)—C(R$^{14}$,R$^{15}$)—Y—,
—X—C(R$^{12}$,R$^{13}$)—C(R$^{14}$,R$^{15}$)—C(R$^{16}$,R$^{17}$)—,
—C(R$^{12}$,R$^{13}$)—X—C(R$^{14}$,R$^{15}$)—C(R$^{16}$,R$^{17}$)—,
—X—N(R$^{20}$)—X—,
—S—N(R$^{20}$)—X—, —C(R$^{12}$,R$^{13}$)—N(R$^{20}$)—X—,
—X—N(R$^{20}$)—Y—N(R$^{21}$)—or
—N(R$^{20}$)—X—N=C(R$^{12}$)—, X and Y independently of one another are each oxygen, sulfur, —SO—, —SO$_2$—, —CO—, —C(R$^{18}$,R$^{19}$)—or —NR$^{20}$— and R$^{12}$ to R$^{19}$ are each hydrogen, halogen, hydroxyl, $C_1$–$C_4$-alkyl, $C_1$–$C_4$-alkoxy, $C_1$–$C_4$-alkylthio, $C_1$–$C_4$-alkylamino, di-($C_1$–$C_4$-alkyl)amino or phenyl and R$^{20}$ and R$^{21}$ are each hydrogen, $C_1$–$C_4$-alkyl, $C_1$–$C_4$-alkoxy, ($C_1$–$C_4$-alkyl)-carbonyl, phenyl or benzoyl;

Ph is phenyl which may be unsubstituted or, if desired, may carry from one to three substituents selected from the group consisting of halogen, cyano, nitro, —S(O)$_n$R$^{22}$, ($C_1$–$C_4$-alkoxy) carbonyl, —SO$_2$—N(R$^{23}$)R$^{24}$, —N(R$^{23}$)—COR$^{24}$, —N(R$^{23}$)—SO$_2$R$^{25}$, $C_1$–$C_4$-alkyl, $C_1$–$C_4$-alkoxy, $C_1$–$C_4$-haloalkyl and $C_1$–$C_4$-haloalkoxy, where the four last-mentioned radicals in turn may carry one or two of the following substituents: $C_1$–$C_4$-alkoxy, $C_1$–$C_4$-alkylthio and/or cyano;

m and n are each 0, 1 or 2;

R$^8$ and R$^{22}$ independently of one another are each $C_1$–$C_4$-alkyl or $C_1$–$C_4$-haloalkyl, where these groups may carry one or two $C_1$–$C_4$-alkoxy, $C_1$–$C_4$-alkylthio and/or cyano radicals;

R$^9$, R$^{10}$, R$^{23}$ and R$^{24}$ independently of one another are each hydrogen, $C_1$–$C_4$-alkyl, $C_1$–$C_4$-haloalkyl, phenyl or phenyl which carries from one to three radicals selected from the group consisting of halogen, $C_1$–$C_4$-alkyl and $C_1$–$C_4$-alkoxy;

R$^{11}$ and R$^{25}$ independently of one another are each $C_1$–$C_4$-alkyl or $C_1$–$C_4$-haloalkyl, where these groups may carry one or two cyano, phenyl and/or benzyl radicals;

R$^2$, R$^3$, R$^4$ and R$^5$ independently of one another are each hydrogen or $C_1$–$C_4$-alkyl;

R$^6$ is hydrogen, $C_1$–$C_4$-alkyl or ($C_1$–$C_4$-alkoxy)carbonyl;

R$^7$ is $C_1$–$C_4$-alkyl, with the proviso that R$^1$ is not mono- or dihalophenyl, and the agriculturally useful salts thereof and the esters of I with $C_1$–$C_{10}$-carboxylic acids or inorganic acids.

The present invention furthermore relates to processes for the preparation of these compounds, their use as herbicides and for regulating plant growth, herbicides and plant growth regulators which contain these compounds as active ingredients, and processes for the preparation of these agents.

Furthermore, the present invention relates to methods for controlling undesirable plant growth and to methods for regulating plant growth.

Herbicidal 2-aroylcyclohexanediones are known from the following publications: EP-A 90262, EP-A 135191, EP-A 186118, EP-A 186119, EP-A 186120, EP-A 319075, WO 90/05712, WO 91/01289, JP-A-03 052862 and JP-A-03 120202.

Furthermore, EP-A 243 313 describes 2-aroylcyclohexanediones of the type similar to the compounds I, which carry a 1-alkylthiocycloalkyl radical in the 5 position.

However, the herbicidal and plant growth-regulating properties of the known compounds are satisfactory only to a limited extent, particularly in the case of low application rates and application concentrations.

It is an object of the present invention to provide further 2-aroylcyclohexanediones having improved properties.

We have found that this object is achieved by the 2-aroylcyclohexanediones of the formula I which are defined at the outset. We have also found processes for the preparation of these compounds, their use as herbicides or plant growth regulators, herbicides and plant growth regulators which contain the compounds I and methods for controlling undesirable plant growth and for regulating plant growth with these agents.

The terms halogen, $C_1$–$C_4$-alkyl, ($C_1$–$C_4$-alkyl) carbonyl, $C_1$–$C_4$-alkoxy, ($C_1$–$C_4$-alkoxy) carbonyl, $C_1$–$C_4$-haloalkyl and $C_1$–$C_4$-haloalkoxy used in the definition of substituents R$^1$ to R$^{25}$ are general terms for individual lists of the individual group members. The six last-mentioned carbon chains may be straight-chain or branched. Halogenated substituents preferably carry from one to five identical or different halogen atoms.

For example, the specific meanings are as follows:

halogen: fluorine, chlorine, bromine or iodine, preferably fluorine or chlorine;

$C_1$–$C_4$-alkyl: methyl, ethyl, n-propyl, 1-methylethyl, n-butyl, 1-methylpropyl, 2-methylpropyl or 1,1-dimethylethyl, preferably methyl or ethyl;

$C_1$–$C_4$-haloalkyl: $C_1$–$C_4$-alkyl as stated above, which is partially or completely substituted by fluorine, chlorine and/or bromine, eg. chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 3-chloropropyl, preferably trifluoromethyl, difluoromethyl, 2,2,2-trifluoroethyl or pentafluoroethyl;

$C_1$–$C_4$-alkoxy: methoxy, ethoxy, n-propoxy, 1-methylethoxy, n-butoxy, 1-methylpropoxy, 2-methylpropoxy or 1,1-dimethylethoxy, preferably methoxy or ethoxy;

$C_1$–$C_4$-haloalkoxy: $C_1$–$C_4$-alkoxy as stated above, which is partially or completely substituted by fluorine, chlorine and/or bromine, eg. chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro2-fluoroethoxy, 2-chloro-2,2-difluoroethoxy, 2,2-dichloro-2-fluoroethoxy, 2,2,2-trichloroethoxy, pentafluoroethoxy or 3-chloropropoxy, preferably difluoromethoxy or trifluoromethoxy;

$C_1$–$C_4$-alkylcarbonyl: methylcarbonyl, ethylcarbonyl, n-propylcarbonyl, 1-methylethylcarbonyl, n-butylcarbonyl, 1-methylpropylcarbonyl, 2-methylpropylcarbonyl or 1,1-dimethylethylcarbonyl, preferably methylcarbonyl;

$C_1$–$C_4$-alkoxycarbonyl: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl or 1,1-dimethylethoxycarbonyl, preferably methoxycarbonyl, ethoxycarbonyl or 1,1-dimethylethoxycarbonyl;

$C_1$–$C_4$-alkylamino: methylamino, ethylamino, n-propylamino, 1-methylethylamino, n-butylamino, 1-methylpropylamino, 2-methylpropylamino or 1,1-dimethylethylamino, preferably methylamino or ethylamino; di-($C_1$–$C_4$-alkyl) amino: eg. N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl) amino, N,N-di-(1,1-dimethylethyl)amino, N-ethyl-N-methylamino, N-methyl-N-propylamino, N-methyl- N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methyl-ethyl)amino, N-butyl-N-ethylamino, N-ethyl-N-(1-methylpropyl)amino, N-ethyl- N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl) amino, N-(1,1-dimethylethyl)-N-(1-methylethyl)amino, N-butyl N-(1-methylpropyl)amino, N-butyl-N-(2-methylpropyl)amino, N-butyl-N-(1,1-dimethylethyl)amino, N-(1-methylpropyl)-N-(2-methylpropyl) amino, N-(1,1-dimethylethyl)-N(1-methylpropyl)amino or N-(1,1-dimethylethyl)-N(2-methylpropyl)amino, preferably dimethylamino or diethylamino.

Hetaryl is preferably a 5-membered or 6-membered aromatic heterocyclic structure having an oxygen and a sulfur atom or a 5-membered or 6-membered aromatic heterocyclic structure having from 1 to 3 hetero atoms selected from the group consisting of 3 nitrogen atoms and one oxygen or sulfur atom, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol 5-yl, 1,2,4-triazol-3-yl, 1,3,4-oxadiazol-2-yl, 1,3,4-thiadiazol-2-yl, 1,3,4-triazol-2-yl, 2yl, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin 3-yl, in particular 2-pyridyl, 3-pyridyl and 4-pyridyl.

5-Membered or 6-membered hetaryl rings carry at least one substituent but at most a number of substituents corresponding to the number of substitutable atoms present.

The aryl and hetaryl rings $R^1$ may, if desired, also carry a fused 5-membered or 6-membered ring which may be partially unsaturated or aromatic.

With regard to the use of the 2-aroylcyclohexanediones I as herbicides or for regulating plant growth, A is preferably methylene or ethylene;

$R^1$ is preferably phenyl or a 5-membered or 6-membered hetaryl, each of which carries from one to four, in particular one, two or three, substituents, each substituent being selected from the group consisting of halogen, nitro, —N=N—Ph, —S(O)$_m$R$^8$, ($C_1$–$C_4$-alkoxy) carbonyl, —N(R$^9$)—COR$^{10}$, —N(R$^9$)—SO$_2$—R$^{11}$, —SO$_2$—N(R$^9$)R$^{10}$, $C_1$–$C_4$-alkyl, $C_1$–$C_4$-alkoxy, $C_1$–$C_4$-haloalkyl and $C_1$–$C_4$-haloalkoxy; or of one of the following bicyclic ring systems:

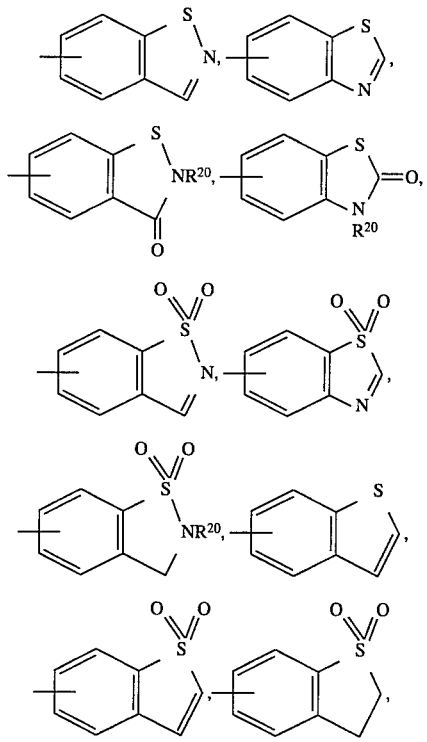

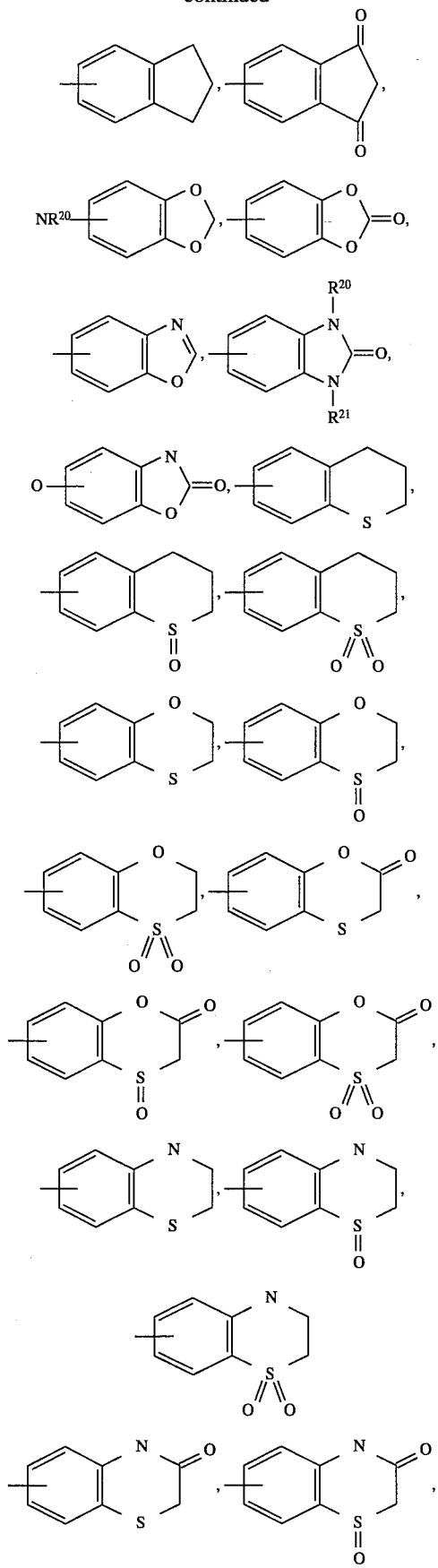

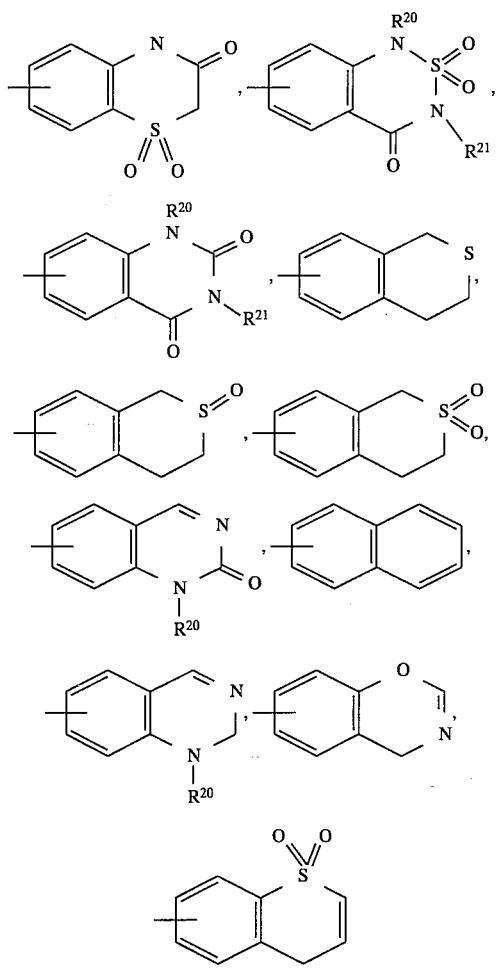

where $R^{20}$ and $R^{21}$ are each preferably hydrogen and/or $C_1$–$C_4$-alkyl;

Ph is preferably phenyl which may be unsubstituted or, if desired, may carry from one to three substituents selected from the group consisting of halogen, cyano, nitro, —S(O)$_n$R$^{22}$, ($C_1$–$C_4$-alkoxy) carbonyl, —SO$_2$—N(R$^{23}$)R$^{24}$, —N(R$^{23}$)—COR$^{24}$, —N(R$^{23}$)—SO$_2$R$^{25}$, $C_1$–$C_4$-alkyl, $C_1$–$C_4$-alkoxy, $C_1$–$C_4$-haloalkyl or $C_1$–$C_4$-haloalkoxy;

m and n independently of one another are each 0, 1 or 2;

$R^8$ and $R^{22}$ are each preferably $C_1$–$C_4$-alkyl or $C_1$–$C_4$-haloalkyl;

$R^9$, $R^{10}$, $R^{23}$ and $R^{24}$ are each preferably hydrogen, $C_1$–$C_4$-alkyl, phenyl or phenyl which carries from one to three radicals selected from the group consisting of halogen, $C_1$–$C_4$-alkyl, $C_1$–$C_4$-haloalkyl and $C_1$–$C_4$-alkoxy;

$R^{11}$ and $R^{25}$ are each preferably $C_1$–$C_4$-alkyl or $C_1$–$C_4$-haloalkyl;

$R^2$ to $R^6$ are each preferably hydrogen and $R^7$ is preferably methyl or ethyl.

Very particularly preferred compounds I are those in which at least one substituent on the phenyl or hetaryl ring $R^1$ is —N=N—Ph, —S(O)$_m$—R$^8$, ($C_1$–$C_4$-alkoxy) carbonyl, —N(R$^9$)—SO$_2$—R$^{11}$, —SO$_2$—N(R$^9$)R$^{10}$, —N(R$^9$)—COR$^{10}$ or $C_1$–$C_4$-haloalkyl.

Owing to their acidic character, the novel 2-aroylcyclohexanediones I can form basic salts or enol esters, the type of salt or ester in general not being important.

Suitable salts of the compounds of the formula I are agriculturally useful salts, for example alkali metal salts, in particular sodium or potassium salt, alkaline earth metal salts, in particular the calcium, magnesium or barium salt, manganese, copper, zinc or iron salts and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

Agriculturally useful esters are understood as meaning the esters of $C_1$–$C_{10}$-fatty acids, in particular $C_1$–$C_6$-alkyl) carboxylic acids, such as methanecarboxylic acid (acetic acid), ethanecarboxylic acid (propionic acid), n-propanecarboxylic acid (butyric acid), 1-methylethanecarboxylic acid (isobutyric acid), n-butylcarboxylic acid, 1-methylpropanecarboxylic acid, 2-methylpropanecarboxylic acid, 1,1-dimethylethanecarboxylic acid, n-pentanecarboxylic acid, 1-methylbutanecarboxylic acid, 2-methylbutanecarboxylic acid, 3-methylbutanecarboxylic acid, 1,1-dimethylpropanecarboxylic acid, 1,2-dimethylpropanecarboxylic acid, 2,2-dimethylpropanecarboxylic acid, 1-ethylpropanecarboxylic acid, benzoic acid and halogen-substituted benzoic acids, n-hexanecarboxylic acid, 1-methylpentanecarboxylic acid, 2-methylpentanecarboxylic acid, 3-methylpentanecarboxylic acid, 4-methylpentanecarboxylic acid, 1,1-dimethylbutanecarboxylic acid, 1,2-dimethylbutanecarboxylic acid, 1,3-dimethylbutanecarboxylic acid, 2,2-dimethylbutanecarboxylic acid, 2,3-dimethylbutanecarboxylic acid, 3,3-dimethylbutanecarboxylic acid, 1-ethylbutanecarboxylic acid, 2-ethylbutanecarboxylic acid, 1,1,2-trimethylpropanecarboxylic acid, 1,2,2-trimethylpropanecarboxylic acid, 1-ethyl-1-methylpropanecarboxylic acid and 1-ethyl-2-methylpropanecarboxylic acid, $C_1$–$C_{10}$-sulfonic acids, in particular $C_1$–$C_6$-alkane sulfonic acids, such as methanesulfonic acid, ethanesulfonic acid, n-propanesulfonic acid, 1-methylethanesulfonic acid, n-butanesulfonic acid, 1-methylpropanesulfonic acid, 2-methylpropanesulfonic acid, 1,1-dimethylethanesulfonic acid, n-pentanesulfonic acid, 1-methylbutanesulfonic acid, 2-methylbutanesulfonic acid, 3-methylbutanesulfonic acid, 1,1-dimethylpropanesulfonic acid, 1,2-dimethylpropanesulfonic acid, 2,2-dimethylpropanesulfonic acid, 1-ethylpropanesulfonic acid, benzenesulfonic acid and halogen-substituted benzenesulfonic acids, n-hexanesulfonic acid, 1-methylpentanesulfonic acid, 2-methylpentanesulfonic acid, 3-methylpentanesulfonic acid, 4-methylpentanesulfonic acid, 1,1-dimethylbutanesulfonic acid, 1,2-dimethylbutanesulfonic acid, 1,3-dimethylbutanesulfonic acid, 2,2-dimethylbutanesulfonic acid, 2,3-dimethylbutanesulfonic acid, 3,3dimethylbutanesulfonic acid, 1-ethylbutanesulfonic acid, 2-ethylbutanesulfonic acid, 1,1,2-trimethylpropanesulfonic acid, 1,2,2-trimethylpropanesulfonic acid, 1-ethyl-1-methylpropanesulfonic acid and 1-ethyl-2-methylpropanesulfonic acid, and $C_1$–$C_{10}$-phosphonic acids, in particular $C_1$–$C_6$-alkanephosphonic acids, such as methanephosphonic acid, ethanephosphonic acid, n-propanephosphonic acid, 1-methylethanephosphonic acid, n-butanephosphonic acid, 1-methylpropanephosphonic acid, 2-methylpropanephosphonic acid, 1,1-dimethylethanephosphonic acid, n-pentanephosphonic acid, 1-methylbutanephosphonic acid, 2-methylbutanephosphonic acid, 3-methylbutanephosphonic acid, 1,1-dimethylpropanephosphonic acid, 1,2-dimethylpropanephosphonic acid, 2,2-dimethylpropanephosphonic acid, 1-ethylpropanephosphonic acid, benzenephosphonic acid and halogen-substituted benzenephosphonic acids, n-hexanephosphonic acid, 1-methylpentanephosphonic acid, 2-methylpentanephosphonic acid, 3-methylpentanephosphonic acid, 4-methylpentanephosphonic acid, 1,1-dimethylbutanephosphonic acid, 1,2-dimethylbutanephosphonic acid, 1,3-dimethylbutanephosphonic acid, 2,2-dimethylbutanephosphonic acid, 2,3-dimethylbutanephosphonic acid, 3,3-dimethylbutanephosphonic acid, 1-ethylbutanephosphonic acid, 2-ethylbutanephosphonic acid, 1,1,2-trimethylpropanephosphonic acid, 1,2,2-trimethylpropanephosphonic acid, 1-ethyl-1-methylpropanephosphonic acid and 1-ethyl-2-methylpropanephosphonic acid.

The 2-aroylcyclohexanediones I can be written in a plurality of tautomeric forms, all of which form the subject of the invention:

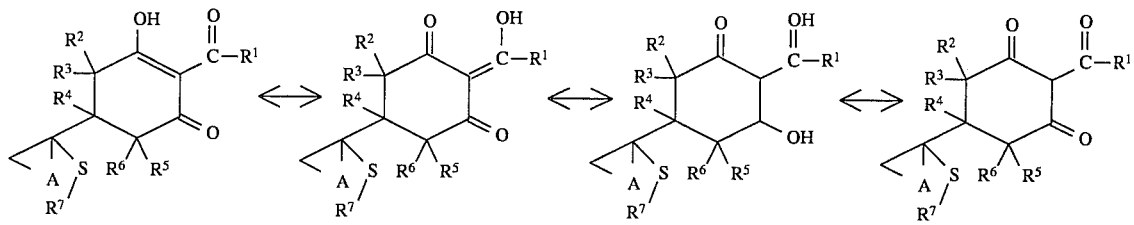

Very particularly preferred 2-aroylcyclohexanediones I ($R^2$ to $R^6$ are each hydrogen) are stated in Table 1 below:

TABLE 1

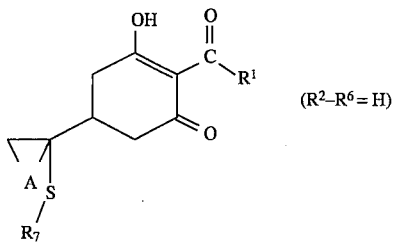

($R^2$–$R^6$ = H)

| No. | $R^1$ | $R^7$ | A |
|---|---|---|---|
| 01 | 2,3-$(CH_3)_2$-4-$(CH_3—SO_2—)$-phenyl | $CH_3$ | $—CH_2—$ |
| 02 | 2-$(CH_3—SO_2—)$-4-(phenyl-N=N—)-phenyl | $CH_3$ | $—CH_2—$ |
| 03 | 2-$(CH_3O—)$-3-$(CH_3OCH_2CH_2O—)$-4-$(CH_3SO_2—)$-phenyl | $CH_3$ | $—CH_2—$ |
| 04 | 2-Chloro-3-$(CH_3O—)$-4-$(CH_3SO_2—)$-phenyl | $CH_3$ | $—CH_2—$ |
| 05 | 2-$(CH_3)$-3-$(CH_3O—)$-4-$(CH_3SO_2—)$-phenyl | $CH_3$ | $—CH_2—$ |
| 06 | 2-Chloro-3-$(CH_3O—)$-4-$(C_2H_5—SO_2—)$-phenyl | $CH_3$ | $—CH_2—$ |
| 07 | 2-$(CH_3)$-3-$(CH_3O—)$-4-$(C_2H_5—SO_2—)$-phenyl | $CH_3$ | $—CH_2—$ |
| 08 | 2-Chloro-4-$(C_2H_5—SO_2—)$-phenyl | $CH_3$ | $—CH_2—$ |
| 09 | 2-Nitro-4-$(C_2H_5SO_2—)$-phenyl | $CH_3$ | $—CH_2—$ |
| 10 | 2-$(C_2H_5SO_2—)$-4-nitro-phenyl | $CH_3$ | $—CH_2—$ |
| 11 | 2-$(C_2H_5SO_2—)$-4-chloro-phenyl | $CH_3$ | $—CH_2—$ |
| 12 | 2,3-$(CH_3)_2$-4-$(C_2H_5SO_2)$-phenyl | $CH_3$ | $—CH_2—$ |
| 13 | 2-Chloro-4-$(CH_3SO_2—)$-phenyl | $CH_3$ | $—CH_2—$ |
| 14 | 4-(Phenyl-N=N—)-phenyl | $CH_3$ | $—CH_2—$ |
| 15 | 2-$(CH_3SO_2—)$-phenyl | $CH_3$ | $—CH_2—$ |
| 16 | 4-$(CH_3SO_2—)$-phenyl | $CH_3$ | $—CH_2—$ |
| 17 | 2-$(CH_3SO_2—)$-4-chloro-phenyl | $CH_3$ | $—CH_2—$ |
| 18 | 2-$(CH_3SO_2—)$-4-nitro-phenyl | $CH_3$ | $—CH_2—$ |
| 19 | 2-Nitro-3-$(CH_3SO_2—)$-phenyl | $CH_3$ | $—CH_2—$ |
| 20 | 2-Chloro-4-nitro-phenyl | $CH_3$ | $—CH_2—$ |
| 21 | 2-Nitro-4-chloro-phenyl | $CH_3$ | $—CH_2—$ |
| 22 | 2-Chloro-3-$(CH_3O—CO—)$-4-$(CH_3SO_2—)$-phenyl | $CH_3$ | $—CH_2—$ |
| 23 | 2-$(CH_3)$-3-$(CH_3O—CO—)$-4-$(CH_3SO_2—)$-phenyl | $CH_3$ | $—CH_2—$ |
| 24 | 2-$(CH_3)$-3-$(CH_3OCH_2CH_2—)$-4-$(C_2H_5SO_2—)$-phenyl | $CH_3$ | $—CH_2—$ |
| 25 | 2-$(C_2H_5)$-3-$(C_2H_5O—CO—)$-4-$(C_2H_5SO_2—)$-phenyl | $CH_3$ | $—CH_2—$ |
| 26 | 2-$(C_2H_5—)$-3-$(CH_3OCH_2CH_2O—CO—)$-4-$(C_2H_5SO_2—)$-phenyl | $CH_3$ | $—CH_2—$ |
| 27 | 2-$(CH_3—)$-3-$(CF_3O—)$-4-$(CH_3SO_2—)$-phenyl | $CH_3$ | $—CH_2—$ |
| 28 | 2-$(CH_3)$-3-$(CH_3O—)$-4-$(CF_3—CH_2OSO_2—)$-phenyl | $CH_3$ | $—CH_2—$ |
| 29 | 2-Nitro-4-[$N(CH_3)_2—SO_2—$]-phenyl | $CH_3$ | $—CH_2—$ |
| 30 | 2-Nitro-4-$(CH_3SO_2NH—)$-phenyl | $CH_3$ | $—CH_2—$ |
| 31 | 2-Chloro-4-[$N(CH_3)_2—SO_2—$]-phenyl | $CH_3$ | $—CH_2—$ |
| 32 | 2-Chloro-4-$(CH_3SO_2NH—)$-phenyl | $CH_3$ | $—CH_2—$ |
| 33 | 2-Chloro-3-$(CH_3OCH_2CH_2O—)$-4-$(C_2H_5SO_2—)$-phenyl | $CH_3$ | $—CH_2—$ |
| 34 | 2-Chloro-3-$(C_2H_5OCH_2CH_2O—)$-4-$(C_2H_5SO_2—)$-phenyl | $CH_3$ | $—CH_2—$ |
| 35 | 2-$(CH_3)$-3-$(C_2H_5OCH_2CH_2O—)$-4-$(C_2H_5SO_2—)$-phenyl | $CH_3$ | $—CH_2—$ |
| 36 | 2-$(NCCH_2CH_2—)$-3-$(CH_3O—)$-4-$(CH_3SO_2—)$-phenyl | $CH_3$ | $—CH_2—$ |
| 37 | 2-Chloro-3-$(CH_3S—)$-4-$(CH_3SO_2—)$-phenyl | $CH_3$ | $—CH_2—$ |
| 38 | 2-$(CH_3)$-3-$(CH_3S—)$-4-$(CH_3SO_2—)$-phenyl | $CH_3$ | $—CH_2—$ |
| 39 | 2-Bromo-3-$(CH_3O—CO—)$-4-$(C_2H_5SO_2—)$-phenyl | $CH_3$ | $—CH_2—$ |
| 40 | 2-$(CH_3SO_2—)$-3-$(CF_3O—)$-4-[$CH_3CON(CH_3)—$]-phenyl | $CH_3$ | $—CH_2—$ |
| 41 | 2-Chloro-3-[$(CH_3)_2CHSO_2—$]-4-(phenyl-$NHSO_2—$)-phenyl | $CH_3$ | $—CH_2—$ |
| 42 | 2-$(CH_3)$-3-$(CH_3SCH_2CH_2O—)$-4-$CH_3NHSO_2—$-phenyl | $CH_3$ | $—CH_2—$ |
| 43 | 2-Chloro-4-(phenyl-N=N—)-phenyl | $CH_3$ | $—CH_2—$ |
| 44 | 2-$(CH_3SO_2—)$-4-cyano-phenyl | $CH_3$ | $—CH_2—$ |
| 45 | 2-Bromo-4-$(CH_3SO_2—)$-phenyl | $CH_3$ | $—CH_2—$ |
| 46 | 2-$(CH_3SO_2—)$-4-bromo-phenyl | $CH_3$ | $—CH_2—$ |
| 47 | 2-$(CH_3)$-3-$(CH_3O—)$-4-$(NH_2SO_2—)$-phenyl | $CH_3$ | $—CH_2—$ |
| 48 | 2-$(CH_3)$-3-$(CH_3O—)$-4-$(CH_3NHSO_2—)$-phenyl | $CH_3$ | $—CH_2—$ |
| 49 | 2,3-Dichloro-4-$(CH_3SO_2—)$-phenyl | $CH_3$ | $—CH_2—$ |
| 50 | 2-Chloro-3-$(CH_3OCH_2—)$-4-$(CH_3SO_2—)$-phenyl | $CH_3$ | $—CH_2—$ |
| 51 | 2-Bromo-4-(phenyl-N=N—)-phenyl | $CH_3$ | $—CH_2—$ |
| 52 | 2-Chloro-3-$(CH_3O—)$-4-(phenyl-N=N—)-phenyl | $CH_3$ | $—CH_2—$ |
| 53 | 2,3-$(CH_3)_2$-4-$(CH_3—SO_2—)$-phenyl | $C_2H_5$ | $—CH_2—$ |
| 54 | 2-$(CH_3—SO_2—)$-4-(phenyl-N=N—)-phenyl | $C_2H_5$ | $—CH_2—$ |
| 55 | 2-$(CH_3O—)$-3-$(CH_3OCH_2CH_2O—)$-4-$(CH_3SO_2—)$-phenyl | $C_2H_5$ | $—CH_2—$ |
| 56 | 2-Chloro-3-$(CH_3O—)$-4-$(CH_3SO_2—)$-phenyl | $C_2H_5$ | $—CH_2—$ |
| 57 | 2-$(CH_3)$-3-$(CH_3O—)$-4-$(CH_3SO_2—)$-phenyl | $C_2H_5$ | $—CH_2—$ |

TABLE 1-continued (R²–R⁶ = H)

| No. | R¹ | R⁷ | A |
|---|---|---|---|
| 58 | 2-Chloro-3-($CH_3O-$)-4-($C_2H_5SO_2-$)-phenyl | $C_2H_5$ | $-CH_2-$ |
| 59 | 2-($CH_3$)-3-($CH_3O-$)-4-($C_2H_5SO_2-$)-phenyl | $C_2H_5$ | $-CH_2-$ |
| 60 | 2-Chloro-4-($C_2H_5SO_2-$)-phenyl | $C_2H_5$ | $-CH_2-$ |
| 61 | 2-Nitro-4-($C_2H_5SO_2-$)-phenyl | $C_2H_5$ | $-CH_2-$ |
| 62 | 2-($C_2H_5SO_2-$)-4-nitro-phenyl | $C_2H_5$ | $-CH_2-$ |
| 63 | 2-($C_2H_5SO_2-$)-4-chloro-phenyl | $C_2H_5$ | $-CH_2-$ |
| 64 | 2,3-($CH_3$)$_2$-4-($C_2H_5SO_2$)-phenyl | $C_2H_5$ | $-CH_2-$ |
| 65 | 2-Chloro-4-($CH_3SO_2-$)-phenyl | $C_2H_5$ | $-CH_2-$ |
| 66 | 4-(Phenyl-N=N-)-phenyl | $C_2H_5$ | $-CH_2-$ |
| 67 | 2-($CH_3SO_2-$)-phenyl | $C_2H_5$ | $-CH_2-$ |
| 68 | 4-($CH_3SO_2-$)-phenyl | $C_2H_5$ | $-CH_2-$ |
| 69 | 2-($CH_3SO_2-$)-4-chloro-phenyl | $C_2H_5$ | $-CH_2-$ |
| 70 | 2-($CH_3SO_2-$)-4-nitro-phenyl | $C_2H_5$ | $-CH_2-$ |
| 71 | 2-Nitro-4-($CH_3SO_2-$)-phenyl | $C_2H_5$ | $-CH_2-$ |
| 72 | 2-Chloro-4-nitro-phenyl | $C_2H_5$ | $-CH_2-$ |
| 73 | 2-Nitro-4-chlor-phenyl | $C_2H_5$ | $-CH_2-$ |
| 74 | 2-Chloro-3-($CH_3O-CO-$)-4-($CH_3SO_2-$)-phenyl | $C_2H_5$ | $-CH_2-$ |
| 75 | 2-($CH_3$)-3-($CH_3O-CO-$)-4-($CH_3SO_2-$)-phenyl | $C_2H_5$ | $-CH_2-$ |
| 76 | 2-($CH_3$)-3-($CH_3OCH_2CH_2-$)-4-($C_2H_5SO_2-$)-phenyl | $C_2H_5$ | $-CH_2-$ |
| 77 | 2-($C_2H_5$)-3-($C_2H_5O-CO-$)-4-($C_2H_5SO_2-$)-phenyl | $C_2H_5$ | $-CH_2-$ |
| 78 | 2-($C_2H_5$)-3-($CH_3OCH_2CH_2O-CO-$)-4-($C_2H_5SO_2-$)-phenyl | $C_2H_5$ | $-CH_2-$ |
| 79 | 2-($CH_3-$)-3-($CF_3O-$)-4-($CH_3SO_2-$)-phenyl | $C_2H_5$ | $-CH_2-$ |
| 80 | 2-($CH_3$)-3-($CH_3O-$)-4-($CF_3-CH_2OSO_2-$)-phenyl | $C_2H_5$ | $-CH_2-$ |
| 81 | 2-Nitro-4-[$N(CH_3)_2-SO_2-$]-phenyl | $C_2H_5$ | $-CH_2-$ |
| 82 | 2-Nitro-4-($CH_3SO_2NH-$)-phenyl | $C_2H_5$ | $-CH_2-$ |
| 83 | 2-Chloro-4-[$N(CH_3)_2-SO_2-$]-phenyl | $C_2H_5$ | $-CH_2-$ |
| 84 | 2-Chloro-4-($CH_3SO_2NH-$)-phenyl | $C_2H_5$ | $-CH_2-$ |
| 85 | 2-Chloro-3-($CH_3OCH_2CH_2O-$)-4-($C_2H_5SO_2-$)-phenyl | $C_2H_5$ | $-CH_2-$ |
| 86 | 2-Chloro-3-($C_2H_5OCH_2CH_2O-$)-4-($C_2H_5SO_2-$)-phenyl | $C_2H_5$ | $-CH_2-$ |
| 87 | 2-($CH_3$)-3-($C_2H_5OCH_2CH_2O-$)-4-($C_2H_5SO_2-$)-phenyl | $C_2H_5$ | $-CH_2-$ |
| 88 | 2($NCCH_2CH_2-$)-3-($CH_3O-$)-4-($CH_3SO_2-$)-phenyl | $C_2H_5$ | $-CH_2-$ |
| 89 | 2-Chloro-3-($CH_3S-$)-4-($CH_3SO_2-$)-phenyl | $C_2H_5$ | $-CH_2-$ |
| 90 | 2-($CH_3$)-3-($CH_3S-$)-4-($CH_3SO_2-$)-phenyl | $C_2H_5$ | $-CH_2-$ |
| 91 | 2-Bromo-3-($CH_3O-CO-$)-4-($C_2H_5SO_2-$)-phenyl | $C_2H_5$ | $-CH_2-$ |
| 92 | 2-($CH_3SO_2-$)-3-($CF_3O-$)-4-[$CH_3CON(CH_3)-$]-phenyl | $C_2H_5$ | $-CH_2-$ |
| 93 | 2-Chloro-3-[$(CH_3)_2CHSO_2-$]-4-(phenyl-$NHSO_2-$)-phenyl | $C_2H_5$ | $-CH_2-$ |
| 94 | 2-($CH_3$)-3-($CH_3SCH_2CH_2O-$)-4-($CH_3NHSO_2-$)-phenyl | $C_2H_5$ | $-CH_2-$ |
| 95 | 2-Chloro-4-(phenyl-N=N-)-phenyl | $C_2H_5$ | $-CH_2-$ |
| 96 | 2-($CH_3SO_2-$)-4-cyano-phenyl | $C_2H_5$ | $-CH_2-$ |
| 97 | 2-Bromo-4-($CH_3SO_2-$)-phenyl | $C_2H_5$ | $-CH_2-$ |
| 98 | 2-($CH_3SO_2-$)-4-bromo-phenyl | $C_2H_5$ | $-CH_2-$ |
| 99 | 2-($CH_3$)-3-($CH_3O-$)-4-($NH_2SO_2-$)-phenyl | $C_2H_5$ | $-CH_2-$ |
| 100 | 2-($CH_3$)-3-($CH_3O-$)-4($CH_3NHSO_2-$)-phenyl | $C_2H_5$ | $-CH_2-$ |
| 101 | 2,3-Dichloro-4-($CH_3SO_2-$)-phenyl | $C_2H_5$ | $-CH_2-$ |
| 102 | 2-Chloro-3-($CH_3OCH_2-$)-4-($CH_3SO_2-$)-phenyl | $C_2H_5$ | $-CH_2-$ |
| 103 | 2-Bromo-4-(phenyl-N=N-)-phenyl | $C_2H_5$ | $-CH_2-$ |
| 104 | 2-Chloro-3-($CH_3O-$)-4-(phenyl-N=N-)-phenyl | $C_2H_5$ | $-CH_2-$ |
| 105 | 2,3-($CH_3$)$_2$-4-($CH_3-SO_2-$)-phenyl | $CH_3$ | $-(CH_2)_2-$ |
| 106 | 2-($CH_3-SO_2-$)-4-(phenyl-N=N-)-phenyl | $CH_3$ | $-(CH_2)_2-$ |
| 107 | 2-($CH_3O-$)-3-($CH_3OCH_2CH_2O-$)-4-($CH_3SO_2-$)-phenyl | $CH_3$ | $-(CH_2)_2-$ |
| 108 | 2-Chloro-3-($CH_3O-$)-4-($CH_3SO_2-$)-phenyl | $CH_3$ | $-(CH_2)_2-$ |
| 109 | 2-($CH_3$)-3-($CH_3O-$)-4-($CH_3SO_2-$)-phenyl | $CH_3$ | $-(CH_2)_2-$ |
| 110 | 2-Chloro-3-($CH_3O-$)-4-($C_2H_5SO_2-$)-phenyl | $CH_3$ | $-(CH_2)_2-$ |
| 111 | 2-($CH_3$)-3-($CH_3O-$)-4-($C_2H_5SO_2-$)-phenyl | $CH_3$ | $-(CH_2)_2-$ |
| 112 | 2-Chloro-4-($C_2H_5SO_2-$)-phenyl | $CH_3$ | $-(CH_2)_2-$ |
| 113 | 2-Nitro-4-($C_2H_5SO_2-$)-phenyl | $CH_3$ | $-(CH_2)_2-$ |

TABLE 1-continued ($R^2$–$R^6$ = H)

| No. | $R^1$ | $R^7$ | A |
|---|---|---|---|
| 114 | 2-($C_2H_5SO_2$—)-4-nitro-phenyl | $CH_3$ | —$(CH_2)_2$— |
| 115 | 2-($C_2H_5SO_2$—)-4-chloro-phenyl | $CH_3$ | —$(CH_2)_2$— |
| 116 | 2,3-($CH_3$)$_2$-4-($C_2H_5SO_2$—)-phenyl | $CH_3$ | —$(CH_2)_2$— |
| 117 | 2-Chloro-4-($CH_3SO_2$—)-phenyl | $CH_3$ | —$(CH_2)_2$— |
| 118 | 4-(Phenyl-N=N—)-phenyl | $CH_3$ | —$(CH_2)_2$— |
| 119 | 2-($CH_3SO_2$—)-phenyl | $CH_3$ | —$(CH_2)_2$— |
| 120 | 4-($CH_3SO_2$—)-phenyl | $CH_3$ | —$(CH_2)_2$— |
| 121 | 2-($CH_3SO_2$—)-4-chloro-phenyl | $CH_3$ | —$(CH_2)_2$— |
| 122 | 2-($CH_3SO_2$—)-4-nitro-phenyl | $CH_3$ | —$(CH_2)_2$— |
| 123 | 2-Nitro-4-($CH_3SO_2$—)-phenyl | $CH_3$ | —$(CH_2)_2$— |
| 124 | 2-Chloro-4-nitro-phenyl | $CH_3$ | —$(CH_2)_2$— |
| 125 | 2-Nitro-4-chloro-phenyl | $CH_3$ | —$(CH_2)_2$— |
| 126 | 2-Chloro-3-($CH_3O$—CO—)-4-($CH_3SO_2$—)-phenyl | $CH_3$ | —$(CH_2)_2$— |
| 127 | 2-($CH_3$)-3-($CH_3O$—CO—)-4-($CH_3SO_2$—)-phenyl | $CH_3$ | —$(CH_2)_2$— |
| 128 | 2-($CH_3$)-3-($CH_3OCH_2CH_2$—)-4-($C_2H_5SO_2$—)-phenyl | $CH_3$ | —$(CH_2)_2$— |
| 129 | 2-($C_2H_5$—)-3-($C_2H_5O$—CO—)-4-($C_2H_5SO_2$—)-phenyl | $CH_3$ | —$(CH_2)_2$— |
| 130 | 2-($C_2H_5$—)-3-($CH_3OCH_2CH_2O$—CO—)-4-($C_2H_5SO_2$—)-phenyl | $CH_3$ | —$(CH_2)_2$— |
| 131 | 2-($CH_3$)-3-($CF_3O$—)-4-($CH_3SO_2$—)-phenyl | $C_2H_5$ | —$(CH_2)_2$— |
| 132 | 2-($CH_3$)-3-($CH_3O$—)-4-($CF_3$—$CH_2OSO_2$—)-phenyl | $C_2H_5$ | —$(CH_2)_2$— |
| 133 | 2-Nitro-4-[N($CH_3$)$_2$—$SO_2$—]-phenyl | $C_2H_5$ | —$(CH_2)_2$— |
| 134 | 2-Nitro-4-($CH_3SO_2NH$—)-phenyl | $C_2H_5$ | —$(CH_2)_2$— |
| 135 | 2-Chloro-4-[N($CH_3$)$_2$—$SO_2$—]-phenyl | $C_2H_5$ | —$(CH_2)_2$— |
| 136 | 2-Chloro-4-($CH_3SO_2NH$—)-phenyl | $C_2H_5$ | —$(CH_2)_2$— |
| 137 | 2-Chloro-3-($CH_3OCH_2CH_2O$—)-4-($C_2H_5SO_2$—)-phenyl | $C_2H_5$ | —$(CH_2)_2$— |
| 138 | 2-Chloro-3-($C_2H_5OCH_2CH_2O$—)-4-($C_2H_5SO_2$—)-phenyl | $C_2H_5$ | —$(CH_2)_2$— |
| 139 | 2-($CH_3$)-3-($C_2H_5OCH_2CH_2O$—)-4-($C_2H_5SO_2$—)-phenyl | $C_2H_5$ | —$(CH_2)_2$— |
| 140 | 2(NC$CH_2CH_2$—)-3-($CH_3O$—)-4-($CH_3SO_2$—)-phenyl | $C_2H_5$ | —$(CH_2)_2$— |
| 141 | 2-Chloro-3-($CH_3S$—)-4-($CH_3SO_2$—)-phenyl | $C_2H_5$ | —$(CH_2)_2$— |
| 142 | 2-($CH_3$)-3-($CH_3S$—)-4-($CH_3SO_2$—)-phenyl | $C_2H_5$ | —$(CH_2)_2$— |
| 143 | 2-Bromo-3-($CH_3O$—CO—)-4-($C_2H_5SO_2$—)-phenyl | $C_2H_5$ | —$(CH_2)_2$— |
| 144 | 2-($CH_3SO_2$—)-3-($CF_3O$—)-4-[$CH_3CON(CH_3)$—]-phenyl | $C_2H_5$ | —$(CH_2)_2$— |
| 145 | 2-Chloro-3-[($CH_3$)$_2$CH$SO_2$—]-4-(phenyl-NH$SO_2$—)-phenyl | $C_2H_5$ | —$(CH_2)_2$— |
| 146 | 2-($CH_3$)-3($CH_3SCH_2CH_2O$—)-4-($CH_3NHSO_2$—)-phenyl | $C_2H_5$ | —$(CH_2)_2$— |
| 147 | 2-Chloro-4-(phenyl-N=N—)-phenyl | $C_2H_5$ | —$(CH_2)_2$— |
| 148 | 2-($CH_3SO_2$—)-4-cyano-phenyl | $C_2H_5$ | —$(CH_2)_2$— |
| 149 | 2-Bromo-4-($CH_3SO_2$—)-phenyl | $C_2H_5$ | —$(CH_2)_2$— |
| 150 | 2-($CH_3SO_2$—)-4-bromo-phenyl | $C_2H_5$ | —$(CH_2)_2$— |
| 151 | 2-($CH_3$)-3-($CH_3O$—)-4-($NH_2SO_2$—)-phenyl | $C_2H_5$ | —$(CH_2)_2$— |
| 152 | 2-($CH_3$)-3-($CH_3O$—)-4-($CH_3NHSO_2$—)-phenyl | $C_2H_5$ | —$(CH_2)_2$— |
| 153 | 2,3-Dichloro-4-($CH_3SO_2$—)-phenyl | $C_2H_5$ | —$(CH_2)_2$— |
| 154 | 2-Chloro-3-($CH_3OCH_2$—)-4-($CH_3SO_2$—)-phenyl | $C_2H_5$ | —$(CH_2)_2$— |
| 155 | 2-Bromo-4-(phenyl-N=N—)-phenyl | $C_2H_5$ | —$(CH_2)_2$— |
| 156 | 2-Chloro-3-($CH_3O$—)-4-(phenyl-N=N—)-phenyl | $C_2H_5$ | —$(CH_2)_2$— |
| 157 | 2,3-($CH_3$)$_2$-4-($CH_3$—$SO_2$—)-phenyl | $C_2H_5$ | —$(CH_2)_2$— |
| 158 | 2-($CH_3$—$SO_2$—)-4-(phenyl-N=N—)-phenyl | $C_2H_5$ | —$(CH_2)_2$— |
| 159 | 2-($CH_3O$—)-3-($CH_3OCH_2CH_2O$—)-4-($CH_3SO_2$—)-phenyl | $C_2H_5$ | —$(CH_2)_2$— |
| 160 | 2-Chloro-3-($CH_3O$—)-4-($CH_3SO_2$—)-phenyl | $C_2H_5$ | —$(CH_2)_2$— |
| 161 | 2-($CH_3$)-3-($CH_3O$—)-4-($CH_3SO_2$—)-phenyl | $C_2H_5$ | —$(CH_2)_2$— |
| 162 | 2-Chloro-3-($CH_3O$—)-4-($C_2H_5SO_2$—)-phenyl | $C_2H_5$ | —$(CH_2)_2$— |
| 163 | 2-($CH_3$)-3-($CH_3O$—)-4-($C_2H_5SO_2$—)-phenyl | $C_2H_5$ | —$(CH_2)_2$— |
| 164 | 2-Chloro-4-($C_2H_5SO_2$—)-phenyl | $C_2H_5$ | —$(CH_2)_2$— |
| 165 | 2-Nitro-4-($C_2H_5SO_2$—)-phenyl | $C_2H_5$ | —$(CH_2)_2$— |
| 166 | 2-($C_2H_5SO_2$—)-4-nitro-phenyl | $C_2H_5$ | —$(CH_2)_2$— |
| 167 | 2-($C_2H_5SO_2$—)-4-chloro-phenyl | $C_2H_5$ | —$(CH_2)_2$— |
| 168 | 2,3-($CH_3$)$_2$-4-($C_2H_5SO_2$)-phenyl | $C_2H_5$ | —$(CH_2)_2$— |
| 169 | 2-Chloro-4-($CH_3SO_2$—)-phenyl | $C_2H_5$ | —$(CH_2)_2$— |

TABLE 1-continued (R²–R⁶ = H)

| No. | R¹ | R⁷ | A |
|-----|----|----|---|
| 170 | 2-(Phenyl-N=N—)-phenyl | $C_2H_5$ | $-(CH_2)_2-$ |
| 171 | 2-($CH_3SO_2-$)-phenyl | $C_2H_5$ | $-(CH_2)_2-$ |
| 172 | 4-($CH_3SO_2-$)-phenyl | $C_2H_5$ | $-(CH_2)_2-$ |
| 173 | 2-($CH_3SO_2-$)-4-chloro-phenyl | $C_2H_5$ | $-(CH_2)_2-$ |
| 174 | 2-($CH_3SO_2-$)-4-nitro-phenyl | $C_2H_5$ | $-(CH_2)_2-$ |
| 175 | 2-Nitro-4-($CH_3SO_2-$)-phenyl | $C_2H_5$ | $-(CH_2)_2-$ |
| 176 | 2-Chloro-4-nitro-phenyl | $C_2H_5$ | $-(CH_2)_2-$ |
| 177 | 2-Nitro-4-chlor-phenyl | $C_2H_5$ | $-(CH_2)_2-$ |
| 178 | 2-Chloro-3-($CH_3O-CO-$)-4-($CH_3SO_2-$)-phenyl | $C_2H_5$ | $-(CH_2)_2-$ |
| 179 | 2-($CH_3$)-3-($CH_3O-CO-$)-4-($CH_3SO_2-$)-phenyl | $C_2H_5$ | $-(CH_2)_2-$ |
| 180 | 2-($CH_3$)-3-($CH_3OCH_2CH_2-$)-4-($C_2H_5SO_2-$)-phenyl | $C_2H_5$ | $-(CH_2)_2-$ |
| 181 | 2-($C_2H_5$)-3-($C_2H_5O-CO-$)-4-($C_2H_5SO_2-$)-phenyl | $C_2H_5$ | $-(CH_2)_2-$ |
| 182 | 2-($C_2H_5$)-3-($CH_3OCH_2CH_2O-CO-$)-4-($C_2H_5SO_2-$)-phenyl | $C_2H_5$ | $-(CH_2)_2-$ |
| 183 | 2-($CH_3$)-3-($CF_3O-$)-4-($CH_3SO_2-$)-phenyl | $C_2H_5$ | $-(CH_2)_2-$ |
| 184 | 2-($CH_3$)-3-($CH_3O-$)-4-($CF_3-CH_2OSO_2-$)-phenyl | $C_2H_5$ | $-(CH_2)_2-$ |
| 185 | 2-Nitro-4-[$N(CH_3)_2-SO_2-$]-phenyl | $C_2H_5$ | $-(CH_2)_2-$ |
| 186 | 2-Nitro-4-($CH_3SO_2NH-$)-phenyl | $C_2H_5$ | $-(CH_2)_2-$ |
| 187 | 2-Chloro-4-[$N(CH_3)_2-SO_2-$]-phenyl | $C_2H_5$ | $-(CH_2)_2-$ |
| 188 | 2-Chloro-4-($CH_3SO_2NH-$)-phenyl | $C_2H_5$ | $-(CH_2)_2-$ |
| 189 | 2-Chloro-3-($CH_3OCH_2CH_2O-$)-4-($C_2H_5SO_2-$)-phenyl | $C_2H_5$ | $-(CH_2)_2-$ |
| 190 | 2-Chloro-3-($C_2H_5OCH_2CH_2O-$)-4-($C_2H_5SO_2-$)-phenyl | $C_2H_5$ | $-(CH_2)_2-$ |
| 191 | 2-($CH_3$)-3-($C_2H_5OCH_2CH_2O-$)-4-($C_2H_5SO_2-$)-phenyl | $C_2H_5$ | $-(CH_2)_2-$ |
| 192 | 2($NCCH_2CH_2-$)-3-($CH_3O-$)-4-($CH_3SO_2-$)-phenyl | $C_2H_5$ | $-(CH_2)_2-$ |
| 193 | 2-Chloro-3-($CH_3S-$)-4-($CH_3SO_2-$)-phenyl | $C_2H_5$ | $-(CH_2)_2-$ |
| 194 | 2-($CH_3$)-3-($CH_3S-$)-4-($CH_3SO_2-$)-phenyl | $C_2H_5$ | $-(CH_2)_2-$ |
| 195 | 2-Bromo-3-($CH_3O-CO-$)-4-($C_2H_5SO_2-$)-phenyl | $C_2H_5$ | $-(CH_2)_2-$ |
| 196 | 2-($CH_3SO_2-$)-3-($CF_3O-$)-4-[$CH_3CON(CH_3)-$]-phenyl | $C_2H_5$ | $-(CH_2)_2-$ |
| 197 | 2-Chloro-3-[$(CH_3)_2CHSO_2-$]-4-(phenyl-$NHSO_2-$)-phenyl | $C_2H_5$ | $-(CH_2)_2-$ |
| 198 | 2-($CH_3$)-3-($CH_3SCH_2CH_2O-$)-4-($CH_3NHSO_2-$)-phenyl | $C_2H_5$ | $-(CH_2)_2-$ |
| 199 | 2-Chloro-4-(phenyl-N=N—)-phenyl | $C_2H_5$ | $-(CH_2)_2-$ |
| 200 | 2-($CH_3SO_2-$)-4-cyano-phenyl | $C_2H_5$ | $-(CH_2)_2-$ |
| 201 | 2-Bromo-4-($CH_3SO_2-$)-phenyl | $C_2H_5$ | $-(CH_2)_2-$ |
| 202 | 2-($CH_3SO_2-$)-4-bromo-phenyl | $C_2H_5$ | $-(CH_2)_2-$ |
| 203 | 2-($CH_3$)-3-($CH_3O-$)-4-($NH_2SO_2-$)-phenyl | $C_2H_5$ | $-(CH_2)_2-$ |
| 204 | 2-($CH_3$)-3-($CH_3O-$)-4-($CH_3NHSO_2-$)-phenyl | $C_2H_5$ | $-(CH_2)_2-$ |
| 205 | 2,3-Dichloro-4-($CH_3SO_2-$)-phenyl | $C_2H_5$ | $-(CH_2)_2-$ |
| 206 | 2-Chloro-3-($CH_3OCH_2-$)-4-($CH_3SO_2-$)-phenyl | $C_2H_5$ | $-(CH_2)_2-$ |
| 207 | 2-Bromo-4-(phenyl-N=N—)-phenyl | $C_2H_5$ | $-(CH_2)_2-$ |
| 208 | 2-Chloro-3-($CH_3O-$)-4-(phenyl-N=N—)-phenyl | $C_2H_5$ | $-(CH_2)_2-$ |
| 209 | 2,3-($CH_3$)$_2$-4-($CH_3SO_2-$)-phenyl | $CH(CH_3)_2$ | $-CH_2-$ |
| 210 | 2-($CH_3SO_2-$)-4-(phenyl-N=N—)-phenyl | $CH(CH_3)_2$ | $-CH_2-$ |
| 211 | 2-($CH_3O-$)-3-($CH_3OCH_2CH_2O-$)-4-($CH_3SO_2-$)-phenyl | $C(CH_3)_3$ | $-CH_2-$ |
| 212 | 2-Chloro-3-($CH_3O-$)-4-($CH_3SO_2-$)-phenyl | $C(CH_3)_3$ | $-CH_2-$ |
| 213 | 2-($CH_3$)-3-($CH_3O-$)-4-($CH_3SO_2-$)-phenyl | $CH(CH_3)_2$ | $-(CH_2)_2-$ |
| 214 | 2-Chloro-3-($CH_3O-$)-4-($C_2H_5SO_2-$)-phenyl | $CH(CH_3)_2$ | $-(CH_2)_2-$ |
| 215 | 2-($CH_3$)-3-($CH_3O-$)-4-($C_2H_5SO_2-$)-phenyl | $C(CH_3)_3$ | $-(CH_2)_2-$ |
| 216 | 2-Chloro-4-($C_2H_5SO_2-$)-phenyl | $C(CH_3)_3$ | $-(CH_2)_2-$ |
| 217 | 2-Nitro-4-($C_2H_5SO_2-$)-phenyl | $(CH_2)_3-CH_3$ | $-(CH_2)_2-$ |
| 218 | 2-($C_2H_5SO_2-$)-4-nitro-phenyl | $CH(CH_3)_2$ | $-(CH_2)_3-$ |
| 219 | 2-($C_2H_5SO_2-$)-4-chloro-phenyl | $CH(CH_3)_2$ | $-(CH_2)_3-$ |
| 220 | 2,3-($CH_3$)$_2$-4-($C_2H_5SO_2-$)-phenyl | $(CH_2)_2-CH_3$ | $-(CH_2)_3-$ |
| 221 | 2-Chloro-4-($CH_3SO_2-$)-phenyl | $(CH_2)_2-CH_3$ | $-(CH_2)_2-$ |
| 222 | 2-(Phenyl-N=N—)-phenyl | $CH_3$ | $-(CH_2)_3-$ |
| 223 | 2-($CH_3SO_2-$)-phenyl | $CH_3$ | $-(CH_2)_3-$ |
| 224 | 4-($CH_3SO_2-$)-phenyl | $C_2H_5$ | $-(CH_2)_3-$ |
| 225 | 2-($CH_3SO_2-$)-4-chloro-phenyl | $C_2H_5$ | $-(CH_2)_3-$ |

TABLE 1-continued

[Structural formula with OH, C(=O)R¹ groups on cyclohexanedione ring with A-S-R₇ substituent; (R²–R⁶ = H)]

| No. | R¹ | R⁷ | A |
|---|---|---|---|
| 226 | 2-($CH_3SO_2-$)-4-nitro-phenyl | $CH(CH_3)_2$ | $-CH_2-$ |
| 227 | 2-Nitro-4-($CH_3SO_2-$)-phenyl | $CH(CH_3)_2$ | $-CH_2-$ |
| 228 | 2-Chloro-4-nitro-phenyl | $C(CH_3)_3$ | $-CH_2-$ |
| 229 | 2-Nitro-4-chlor-phenyl | $C(CH_3)_3$ | $-CH_2-$ |
| 230 | 2-Chloro-3-($CH_3O-CO-$)-4-($CH_3SO_2-$)-phenyl | $(CH_2)_2CH_3$ | $-CH_2-$ |
| 231 | 2-($CH_3$)-3-($CH_3O-CO-$)-4-($CH_3SO_2-$)-phenyl | $(CH_2)_2CH_3$ | $-(CH_2)_2-$ |
| 232 | 2-($CH_3$)-3-($CH_3OCH_2CH_2-$)-4-($C_2H_5SO_2-$)-phenyl | $(CH_2)_2CH_3$ | $-(CH_2)_2-$ |
| 233 | 2-($C_2H_5-$)-3-($C_2H_5O-CO-$)-4-($C_2H_5SO_2-$)-phenyl | $C(CH_3)_3$ | $-(CH_2)_3-$ |
| 234 | 2-($C_2H_5-$)-3-($CH_3OCH_2CH_2O-CO-$)-4-($C_2H_5SO_2-$)-phenyl | $C_2H_5$ | $-(CH_2)_4-$ |
| 235 | 2-($CH_3$)-3-($CF_3O-$)-4-($CH_3SO_2-$)-phenyl | $(CH_2)_3-CH_3$ | $-CH_2-$ |
| 236 | 2-($CH_3$)-3-($CH_3O-$)-4-($CF_3-CH_2OSO_2-$)-phenyl | $CH(CH_3)_2$ | $-CH_2-$ |
| 237 | 2-Nitro-4-[$N(CH_3)_2-SO_2-$]-phenyl | $CH_3$ | $-(CH_2)_4-$ |
| 238 | 2-Nitro-4-($CH_3SO_2NH-$)-phenyl | $CH_3$ | $-(CH_2)_4-$ |
| 239 | 2-Chloro-4-[$N(CH_3)_2-SO_2-$]-phenyl | $C_2H_5$ | $-(CH_2)_4-$ |
| 240 | 2-Chloro-4-($CH_3SO_2NH-$)-phenyl | $C(CH_3)_3$ | $-(CH_2)_4-$ |
| 241 | 2-Chloro-3-($CH_3OCH_2CH_2O-$)-4-($C_2H_5SO_2-$)-phenyl | $C(CH_3)_3$ | $-(CH_2)_4-$ |
| 242 | 2-Chloro-3-($C_2H_5OCH_2CH_2O-$)-4-($C_2H_5SO_2-$)-phenyl | $CH(CH_3)_2$ | $-(CH_2)_2-$ |
| 243 | 2-($CH_3$)-3-($C_2H_5OCH_2CH_2O-$)-4-($C_2H_5SO_2-$)-phenyl | $CH(CH_3)_2$ | $-(CH_2)_2-$ |
| 244 | 2($NCCH_2CH_2-$)-3-($CH_3O-$)-4-($CH_3SO_2-$)-phenyl | $C_2H_5$ | $-(CH_2)_2-$ |
| 245 | 2-Chloro-3-($CH_3S-$)-4-($CH_3SO_2-$)-phenyl | $C(CH_3)_3$ | $-(CH_2)_2-$ |
| 246 | 2-($CH_3$)-3-($CH_3S-$)-4-($CH_3SO_2-$)-phenyl | $C(CH_3)_3$ | $-(CH_2)_2-$ |
| 247 | 2-Bromo-3-($CH_3O-CO-$)-4-($C_2H_5SO_2-$)-phenyl | $CH(CH_3)_2$ | $-(CH_2)_3-$ |
| 248 | 2-($CH_3SO_2-$)-3-($CF_3O-$)-4-[$CH_3CON(CH_3)-$]-phenyl | $CH_3$ | $-(CH_2)_3-$ |
| 249 | 2-Chloro-3-[$(CH_3)_2CHSO_2-$]-4-(phenyl-$NHSO_2-$)-phenyl | $CH_3$ | $-(CH_2)_3-$ |
| 250 | 2-($CH_3$)-3-($CH_3SCH_2CH_2O-$)-4-($CH_3NHSO_2-$)-phenyl | $C_2H_5$ | $-(CH_2)_3-$ |
| 251 | 2-Chloro-4-(phenyl-$N=N-$)-phenyl | $C_2H_5$ | $-(CH_2)_3-$ |
| 252 | 2-($CH_3SO_2-$)-4-cyano-phenyl | $CH_3$ | $-(CH_2)_4-$ |
| 253 | 2-Bromo-4-($CH_3SO_2-$)-phenyl | $CH_3$ | $-(CH_2)_4-$ |
| 254 | 2-($CH_3SO_2-$)-4-bromo-phenyl | $CH_3$ | $-(CH_2)_4-$ |
| 255 | 2-($CH_3$)-3-($CH_3O-$)-4-($NH_2SO_2-$)-phenyl | $CH(CH_3)_2$ | $-CH_2-$ |
| 256 | 2-($CH_3$)-3-($CH_3O-$)-4($CH_3NHSO_2-$)-phenyl | $CH(CH_3)_2$ | $-CH_2-$ |
| 257 | 2,3-Dichloro-4-($CH_3SO_2-$)-phenyl | $CH(CH_3)_2$ | $-(CH_2)_2-$ |
| 258 | 2-Chloro-3-($CH_3OCH_2-$)-4-($CH_3SO_2-$)-phenyl | $CH(CH_3)_2$ | $-(CH_2)_3-$ |
| 259 | 2-Bromo-4-(phenyl-$N=N-$)-phenyl | $CH(CH_3)_2$ | $-(CH_2)_4-$ |
| 260 | 2-Chloro-3-($CH_3O-$)-4-(phenyl-$N=N-$)-phenyl | $C(CH_3)_3$ | $-(CH_2)_4-$ |

The novel 2-aroylcyclohexanediones I are obtainable by various methods, for example by reacting a cyclohexanedione of the formula II with an acid derivative of the formula III in the presence of a base (cf. for example EP-A 186 118 and U.S. Pat. No. 4,695,673):

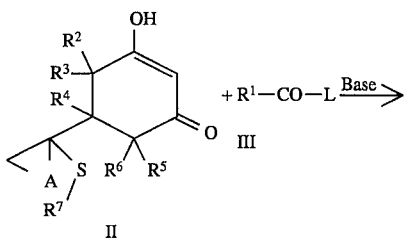

-continued

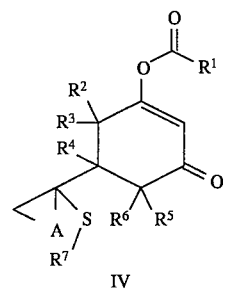

L is a nucleophilic leaving group, such as chloride, bromide or cyanide.

The reaction is carried out in an inert solvent at from 0° C. to the boiling point of the particular solvent, preferably from 0° to 20° C.

Examples of suitable solvents are chlorohydrocarbons, such as methylene chloride, chloroform and dichloroethane, ethers, such as tetrahydrofuran, dioxane and methyl tert-butyl ether, aromatic hydrocarbons, such as benzene and toluene, esters, such as ethyl acetate, or amides, such as dimethylformamide.

Examples of suitable bases are tertiary amines, such as triethylamine, N-methylmorpholine and pyridine.

The base is advantageously used in a roughly equimolar amount, based on the diketone II or the acid derivative III.

The reaction can also be carried out in a heterogeneous system, in which case the diketone II and the base are present in aqueous solution, to which the acid derivative, in a water-immiscible solvent, is added in the presence of a phase transfer catalyst.

Bases which can be used for this purpose are, for example, the alkali metal and alkaline earth metal hydroxides or carbonates, such as sodium hydroxide, potassium hydroxide, sodium carbonate, potassium carbonate, calcium carbonate and calcium hydroxide.

Examples of suitable phase transfer catalysts are ammonium, sulfonium or phosphonium salts, the type of anion being of minor importance. For example, benzyltrimethylammonium hydroxide has proven advantageous.

The resulting enol esters of the formula IV are then subjected to a rearrangement reaction in the presence of a cyanide source and of a base to give the desired compounds of the formula I:

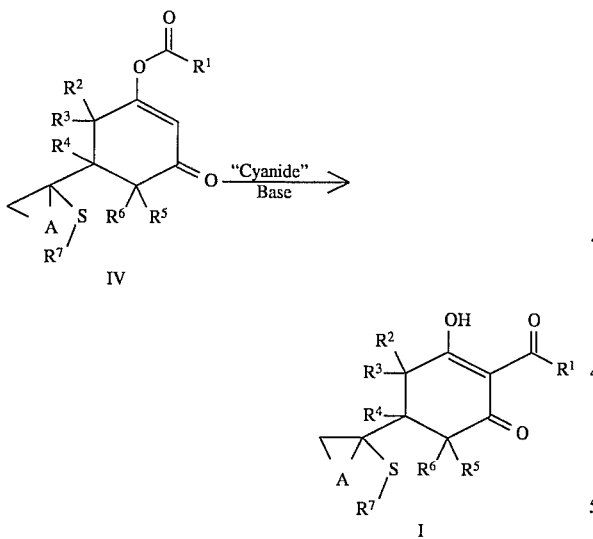

The rearrangement reaction is usually carried out in an inert solvent at from 0° C. to the boiling point of the solvent, preferably from 20° to 40° C.

Examples of suitable solvents are chlorohydrocarbons, such as methylene chloride, chloroform and dichloroethane, ethers, such as tetrahydrofuran, dioxane and methyl tert-butyl ether, aromatic hydrocarbons, such as benzene and toluene, nitriles, such as acetonitrile, esters, such as ethyl acetate, ketones, such as acetone and methyl ethyl ketone, or amides such as dimethylformamide.

Cyanide sources which have proven suitable are, for example, alkali metal cyanides, such as sodium cyanide and potassium cyanide, cyanohydrins, such as acetone cyanohydrin, and trialkylsilyl cyanides, such as trimethylsilyl cyanide.

Usually, a catalytic amount of cyanide, for example from 1 to 10 mol %, based on the enol ester IV, is sufficient. Bases which may be used are, for example, trialkylamines, such as triethylamine, trialkanolamines, such as triethanolamine, and pyridine or inorganic bases, such as alkali metal carbonates and alkali metal phosphates.

It has proven advantageous to add the base in an excess of from 100 to 400 mol %, based on the enol ester IV.

The 2-aroylcyclohexanediones I can be isolated from the reaction mixtures obtained in this process by means of conventional working up methods, for example by extraction or by crystallization.

In the preparation of the compounds I, there is no need to maintain particular conditions with regard to the pressure; in general, the reaction is therefore carried out at atmospheric pressure or under the autogenous pressure of the particular diluent.

The diketones of the formula II are known from EP-A 243 313 or can be prepared in the manner described there. The acid derivatives III required are known or can be obtained by methods known per se {cf. for example The Chemistry of Carboxylic Acids and Esters, S. Patai, editor, J. Wiley and Sons, New York, N.Y.(1969); Survey of Organic Synthesis, C. A. Buehler and D. F. Pearson, J. Wiley and Sons, (1970); Reagents for Organic Synthesis, Vol. I, L. F. Fieser and M. Fieser, pages 767–769 (1967)}.

Alkali metal salts of the compounds I can be obtained by treating I with sodium hydroxide, potassium hydroxide, a sodium alcholate or a potassium alcoholate in aqueous solution or in an organic solvent, such as methanol, ethanol, acetone or toluene.

Other metal salts, for example the manganese, copper, zinc, iron, calcium, magnesium and barium salts, can be prepared from the sodium salts in a conventional manner, as can ammonium, phosphonium, sulfonium or sulfoxonium salts by means of ammonium, phosphonium, sulfonium or sulfoxonium hydroxides.

The esters of the compounds I are likewise obtainable in a conventional manner (cf. for example EP-A 102 823 and EP-A 136 702).

The 2-aroylcyclohexanediones I, their salts and esters or the agents containing these compounds can very readily control weeds and grass weeds in crops such as wheat, rice, corn, soybean and cotton, without damaging the crops. This effect occurs in particular at low application rates.

The compounds I or the herbicides containing them can be applied, for example, in the form of directly sprayable aqueous solutions, powders, suspensions, including concentrated aqueous, oily or other suspensions or dispersions, emulsions, oil dispersions, pastes, dusting agents, broadcasting agents or granules, by spraying, nebulizing, dusting, broadcasting or pouring. The application forms depend on the intended uses; they should in any case ensure very fine distribution of the novel active ingredients.

Suitable inert additives are mineral oil fractions having a medium to high boiling point, such as kerosene or diesel oil, as well as coal tar oils and oils of vegetable or animal origin, aliphatic, cyclic and aromatic hydrocarbons, eg. paraffin, tetrahydronaphthalene, alkylated naphthalenes or derivatives thereof, alkylated benzenes or derivatives thereof, methanol, ethanol, propanol, butanol, cyclohexanol, cyclohexanone or strongly polar solvents, such as N-methylpyrrolidone or water.

Aqueous application forms can be prepared from emulsion concentrates, suspensions, pastes, wettable powders or water-dispersible granules by adding water. For the preparation of emulsions, pastes or oil dispersions, the substances as such or dissolved in an oil or solvent can be homogenized in water by means of wetting agents, adherents, dispersants or emulsifiers. However, it is also possible to prepare concentrates which consist of active ingredient, wetting agents, adherents, dispersants or emulsifiers and possibly solvent or oil and which are suitable for dilution with water.

Suitable surfactants are the alkali metal, alkaline earth metal and ammonium salts of aromatic sulfonic acids, for example ligninsulfonic acid, phenolsulfonic acid, naphthalenesulfonic acid and dibutylnaphthalenesulfonic acid, and of fatty acids, alkylsulfonates, alkylarylsulfonates, alkylsulfates, lauryl ether sulfates and fatty alcohol sulfates, and salts of sulfated hexahepta- and octadecanols and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetal, sorbitol esters, ligninsulfite waste liquors or methylcellulose.

Powders, broadcasting agents and dusting agents can be prepared by mixing or milling the active ingredients together with a solid carrier.

Granules, for example coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulosic powders or other solid carriers.

The formulations contain in general from 0.01 to 95, preferably from 0.5 to 90, % by weight of active ingredient. The active ingredients are used in a purity of from 90 to 100%, preferably from 95 to 100% (according to NMR spectrum).

The novel compounds I may furthermore be formulated, for example, as follows:

I. 20 parts by weight of compound No. 1.4 are dissolved in a mixture which consists of 80 parts by weight of alkylated benzene, 10 parts by weight of the adduct of from 8 to 10 mol of ethylene oxide with 1 mol of N-monoethanololeamide, 5 parts by weight of a calcium salt of dodecylbenzenesulfonic acid and 5 parts by weight of the adduct of 40 mol of ethylene oxide with 1 mol of castor oil. By pouring the solution into 100,000 parts by weight of water and finely distributing therein, an aqueous dispersion which contains 0.02% by weight of the active ingredient is obtained.

II. 20 parts by weight of compound No. 1.5 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of active ingredient No. 1.6 are dissolved in a mixture which consists of 25 parts by weight of cyclohexanone, 65 parts by weight of a mineral oil fraction boiling within the range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of active ingredient No. 1.7 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

V. 3 parts by weight of active ingredient No. 1.19 are mixed with 97 parts by weight of finely divided kaolin. A dusting agent which contains 3% by weight of the active ingredient is obtained in this manner.

VI. 20 parts by weight of active ingredient No. 1.32 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

The herbicides or the active ingredients can be applied by the preemergence or postemergence methods. If the active ingredients are less well tolerated by certain crops, it is possible to use application methods in which the herbicides are sprayed with the aid of the sprayers in such a way that the leaves of the sensitive crops are as far as possible unaffected, whereas the active ingredients reach the leaves of undesirable plants growing underneath or the uncovered soil surface (post-directed, lay-by).

The application rates of active ingredient are from 0.001 to 3.0, preferably from 0.01 to 1.0, kg/ha of active ingredient (a.i.), depending on the aim of control, the season, the target plants and the stage of growth.

In view of the versatility of the application methods, the compounds I or the agents containing them may also be used in a further number of crops for eliminating undesirable plants. For example, the following crops are suitable:

Allium cepa, Ananas comosus, Arachis hypogaea, *Asparagus officinalis*, Beta *vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeumvulgare, Humulus lupulus, Ipomoea bataras, Juglans regia, Lens culinaris, Linum usitatissimum, Lycopersicon lycopersicum,* Malus spp., *Manihot esculenta, Medicago sativa,* Musa spp., *Nicotiana tabacum (N.rustica), Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare),*

*Theobroma cacao, Trifolium pratense, Triticum aestivum, Triticum durum, Vicia faba, Vitis vinifera* and *Zea mays.*

Moreover, the compounds I may be used in crops which have been made highly resistant to the action of I through breeding and/or by using genetic methods.

The compounds of the formula I may furthermore influence the various stages of development of a plant and are therefore used as growth regulators. The wide range of activity of the plant growth regulators is dependent in particular a) on the plant species and variety, b) on the time of application, based on the stage of development of the plant, and on the season, c) on the site of application and method of application (eg. seed dressing, soil treatment, foliage application or trunk injection in the case of trees), d) on climatic factors (eg. temperature, amount of precipitation and also length of day and intensity of light), e) on the soil characteristics (including fertilizer application), f) on the formulation or application form of the active ingredient and g) on the concentrations in which the active ingredient is used.

Of the number of different possible methods of application of the novel plant growth regulators of the formula I in plant cultivation, in agriculture and in horticulture, some are stated below:

A. The compounds which can be used according to the invention permit considerable inhibition of the vegetative growth of the plants, which is evident in particular from a reduction in the growth in length. Accordingly, the treated plants exhibit stunted growth; in addition, a dark leaf coloration is observed. Reduced intensity of the growth of grasses at the edges of roads, in hedges, on canal embankments and on lawn areas such as parks, sports facilities, orchards, ornamental lawns and airfields, proves advantageous in practice, making it possible to reduce the labor-intensive and expensive cutting of grass.

The increase in the stability of crops susceptible to lodging, such as cereals, corn, sunflowers and soybean, is also of economic interest. The resulting shortening and strengthening of the stem reduce or eliminate the danger of lodging of plants under unfavorable weather conditions prior to harvesting.

The use of growth regulators for inhibiting the growth in length and for changing the time of ripening of cotton is also important. This permits completely mechanized harvesting of this important crop.

In the case of fruit trees and other trees, the growth regulators can be used to save pruning costs. In addition, the alternate bearing of fruit trees can be broken by means of growth regulators.

By using growth regulators, it is also possible to increase or inhibit the lateral branching of the plants. This is of interest when, for example in the case of tobacco plants, it is intended to inhibit the formation of side shoots in favor of leaf growth.

Growth regulators can also be used to effect a considerable increase in frost resistance, for example in the case of winter rape. On the one hand, the growth in length and the development to form a leaf or plant mass which is excessively luxuriant (and therefore particularly susceptible to frost) are inhibited. On the other hand, the young rape plants are held back in the vegetative stage of development after sowing and prior to the onset of the winter frosts, in spite of favorable growth conditions. This also eliminates the danger of frost damage to plants which tend toward a premature decline in the inhibition of blooming and toward a transition into the generative phase. In other crops too, for example winter cereals, it is advantageous if the crops are well tillered as a result of treatment with novel compounds in the fall but do not begin the winter with excessively luxuriant foliage. Increased sensitivity to frost and, owing to the relatively small leaf or plant mass, attack by various diseases (for example fungal disease) can thus be prevented. In addition, the inhibition of vegetative growth permits denser planting of the soil in the case of many crops, so that it is possible to achieve a higher yield, based on the soil area.

B. With the growth regulators, it is possible to achieve higher yields of both plant parts and plant ingredients. Thus, it is possible, for example, to induce the growth of larger amounts of buds, blooms, leaves, fruits, seeds, roots and tubers, to increase the content of sugar in sugar beets, sugar cane and citrous fruits, to increase the protein content of cereals or soybean or to stimulate greater latex flow in rubber trees.

The compounds of the formula I can produce increases in the yield by intervening in the metabolism of the plant or by promoting or inhibiting the vegetative and/or generarive growth.

C. Finally, plant growth regulators can be used both for shortening or lengthening the stages of development and for accelerating or slowing down the ripening of the plant parts to be harvested prior to the harvest or of the harvested plant parts after harvesting.

For example, facilitating harvesting is of commercial interest and is permittedby concentrated dropping of fruit or a reduction of the strength of attachment to the tree in the case of citrus fruits, olives or other species and varieties of pomes, drupes and shell fruit. The same mechanism, ie. the promotion of the formation of abscission tissue between fruit part or leaf part and shoot part of the plant is also essential for readily controllable defoliation of useful plants, for example cotton.

D. Furthermore, growth regulators can be used to reduce the water consumption of plants. This is particularly important for agriculturally useful areas which have to be irrigated at high cost, for example in arid or semiarid regions. By using the novel substances, it is possible to reduce the intensity of irrigation and hence to carry out more economical farming. Under the influence of growth regulators, better utilization of the available water is achieved because, inter alia, the extent of opening of the stomata is reduced, a thicker epidermis and cuticle are formed, the root penetration of the soil is improved and the microclimate in the crop is advantageously influenced by more compact growth.

The compounds I are particularly suitable for shortening the stems of crops such as barley, rape and wheat.

The growth regulators of the formula I which are to be used according to the invention can be fed to the crops both via the seed (as seed dressing) and via the soil, ie. through the roots and, particularly preferably, via the foliage by spraying. The preparation of the agents is similar to that of the herbicides (see above).

Owing to the good toleration by plants, the application rate of active ingredient is not critical. The optimum application rate varies depending on the aim of control, the season, the target plants and the stages of growth.

In order to broaden the action spectrum and to achieve synergistic effects, the 2-aroylcyclohexanediones I can be mixed with a large number of members of other groups of herbicidal or growth-regulating active ingredients and applied together with them. For example, suitable herbicidal components of the mixture are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry, for example, a carboxyl or carbimino group in the 2 position, quinoline-carboxylic acid derivatives, imidazolinones, sulfonamides, sulfonylureas, aryloxy- and hetaryloxyphenoxypropionic acids and their salts, esters and amides and others. In the case of growth regulators, chlormequat chloride, ethephon and mepiquat chloride are particularly suitable.

It may also be useful to apply the compounds I, alone or in combination with other herbicides or growth regulators, together as a mixture with further crop protection agents, for example with pesticides or agents for controlling phytopathogenic fungi or bacteria. The miscibility with mineral salt solutions which are used for eliminating nutrient and trace element deficiencies is also of interest. Nonphytotoxic oils and oil concentrates may also be added.

PREPARATION EXAMPLE 2-(2-Chloro-4-methylsulfonylbenzoyl)-5-(1-methylthiocyclopropropyl)-cyclohexane-1,3-dione 0.2 g (2.4 mmol) of acetone cyanohydrin was added to a solution of 1.6 g (3.9 mmol) of 3-(2-chloro-4-methylsulfonylbenzoyloxy)5-(1-methylthiocyclopropyl)-cyclohex-2-enone in 40 ml of anhydrous acetonitrile, after which a solution of 2.0 g (20 mmol) of triethylamine in 10 ml of acetonitrile was added dropwise at about 20° C. The reaction mixture was then stirred for 3 hours at about 20° C. and then poured onto 30 ml of cold 3% strength by weight hydrochloric acid. After extraction with 80 ml of methyl tert-butyl ether, the organic phase was extracted with four times 50 ml of 5% strength by weight aqueous potassium carbonate solution. The combined alkaline extracts were acidified with concentrated hydrochloric acid to a pH of 1 while cooling with ice. The desired product was obtained from this solution by extracting twice with 100 ml of methyl tert-butyl ether and was finally dried and evaporated down. Yield: 1.2 g (75%); mp.: 148°–152° C.

Intermediate:

0.5 g (5 mmol) of triethylamine was added to a solution of 1 g (5 mmol) of 5-(1-methylthiocyclopropyl)-cyclohexane-1,3-dione in 20 ml of anhydrous tetrahydrofuran in the absence of moisture, after which a solution of 1.3 g (5 mmol) of 2-chloro-4-methylsulfonylbenzoyl chloride in 10 ml of anhydrous tetrahydrofuran was added dropwise at 0° C. After the end of the addition, the reaction mixture was stirred for a further 12 hours at about 20° C., after which 80 ml of methylene chloride were added. For working up, the organic phase was washed with 40 ml of water, with 40 ml of semiconcentrated aqueous sodium carbonate solution and again with water, finally dried with sodium sulfate and evaporated down. Yield: 1.7 g (81%) of 3-(2-chloro-4-methylsulfonylbenzoyloxy)-5-(1-methylthiocyclopropyl)-cyclohex-2-enone.

Further 2-aroylcyclohexanediones I, which were prepared or can be prepared in the same manner, are shown in Table 2 below:

TABLE 2

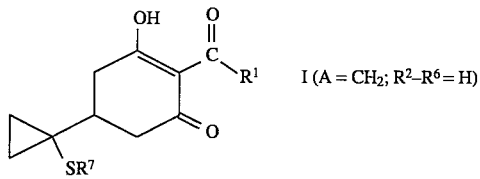

I (A = CH$_2$; R$^2$–R$^6$ = H)

| No. | R$^1$ | R$^7$ | Physical data ($^1$H-NMR: δ[ppm]) |
|---|---|---|---|
| I.1 | 2-Chloro-4-(CH$_3$—SO$_2$—)phenyl | CH$_3$ | 0.78(m, 2H); 1.02(m, 2H); 1.65(m, 1H); 2.13(s, 3H); 3.09(s, 3H); 7.35(d, 1H); 7.9(dd, 1H); 7.97(d, 1H) |
| I.2 | 4-(Phenyl—N=N—)phenyl | CH$_3$ | 0.79(m, 2H); 1.0(m, 2H); 2.12(m, 3H); 7.5(m, 3H); 7.66(d, 2H); 7.9(m, 4H) |
| I.3 | 2-(CH$_3$—SO$_2$—)phenyl | CH$_3$ | 0.75(m, 2H); 0.96(m, 2H); 1.68(m, 1H); 2.1(s, 3H); 3.09(s, 3H); 7.19(dd, 1H); 7.62(m, 2H) |
| I.4 | 2-(CH$_3$—SO$_2$—)-4-chlorophenyl | CH$_3$ | 0.76(m, 2H); 0.99(m, 2H); 2.11(s, 3H), |

TABLE 2-continued

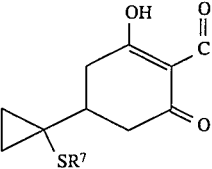

I (A = CH$_2$; R$^2$–R$^6$ = H)

| No. | R$^1$ | R$^7$ | Physical data ($^1$H-NMR: δ[ppm]) |
|---|---|---|---|
| I.5 | 2-Chloro-(3-C$_2$H$_5$O—)-(4-C$_2$H$_5$—SO$_2$—)-phenyl | CH$_3$ | 3.14(s, 3H); 7.13(d, 1H); 7.6(dd, 1H); 7.99(d, 1H); 0.77(m, 2H); 1.0(m, 1H); 2.14(s, 3H); 3.46(q, 2H); 7.06(d, 1H); 7.91(d, 1H) |
| I.6 | 2-Nitro-(4-CH$_3$—SO$_2$—)phenyl | CH$_3$ | 0.75(m, 2H); 1.0(m, 2H); 2.09(s, 3H); 3.18(s, 3H); 7.45(d, 1H); 8.27(dd, 1H); 8.78(d, 1H) |
| I.7 | 2-(CH$_3$—SO$_2$—)-4-nitrophenyl | CH$_3$ | 0.77(m, 2H); 1.0(m, 2H); 2.1(s, 3H); 3.18(s, 3H); 7.39(d, 1H); 8.48(dd, 1H); 8.85(d, 1H) |
| I.8 | 2-Chloro-4-nitrophenyl | CH$_3$ | 0.78(m, 2H); 1.02(m, 2H); 2.12(s, 3H); 7.33(d, 1H); 8.2(dd, 1H); 8.28(d, 1H) |
| I.9 | 2-Nitro-4-chlorophenyl | CH$_3$ | 0.77(m, 2H); 0.99(m, 2H); 2.05(s, 3H); 7.18(d, 1H); 7.68(dd, 1H); 8.2(d, 1H) |
| I.10 | 2-Methyl-3-methoxy-4-(CH$_3$—SO$_2$—)phenyl | CH$_3$ | 0.79(m, 2H); 1.0(m, 2H); 2.12(s, 3H); 2.2(s, 3H); 3.22(s, 3H); 3.91(s, 3H); 6.95(d, 1H); 7.7(d, 1H) |
| I.11 | 2-Chloro-4-nitrophenyl | C$_2$H$_5$ | 0.77(m, 2H); 1.02(m, 2H); 1.20(t, 3H); 2.61(q, 2H); 7.33(d, 1H); 8.2(dd, 1H); 8.28(d, 1H) |
| I.12 | 2-Methyl-3-methoxy-4-(CH$_3$—SO$_2$—)phenyl | C$_2$H$_5$ | 0.77(m, 2H); 1.02(m, 2H); 1.2(t, 3H); 2.2(s, 3H); 2.61(q, 2H); 3.24(s, 3H); 3.93(s, 3H); 6.95(d, 1H); 7.83(d, 1H) |
| I.13 | 2-(CH$_3$—SO$_2$—)phenyl | C$_2$H$_5$ | 0.75(m, 2H); 1.0(m, 2H); 1.19(t, 3H); 2.61(q, 2H); 3.12(s, 3H); |

TABLE 2-continued

[Structure: cyclohexanone with OH, C(=O)R¹, and a cyclopropyl group bearing SR⁷]  I (A = CH₂; R²–R⁶ = H)

| No. | R¹ | R⁷ | Physical data (¹H-NMR: δ[ppm]) |
|---|---|---|---|
| I.14 | 2-(CH₃—SO₂—)-4-nitrophenyl | C₂H₅ | 7.18(dd, 1H); 7.6(m, 2H); 8.0(dd, 1H) 0.73(m, 2H); 1.0(m, 2H); 1.2(t, 3H); 2.58(q, 2H); 3.15(s, 3H); 7.38(d, 1H); 8.46(dd, 1H); 8.83(d, 1H) |
| I.15 | 2-Nitro-4-(CH₃—SO₂—)phenyl | C₂H₅ | 0.77(m, 2H); 1.02(m, 2H); 1.21(t, 3H); 2.6(q, 2H); 3.18(s, 3H); 7.45(d, 1H); 8.27(dd, 1H); 8.76(d, 1H) |
| I.16 | 2-Chloro-4-(CH₃—SO₂—)phenyl | C₂H₅ | 0.78(m, 2H); 1.03(m, 2H); 1.2(t, 3H); 2.62(q, 2H); 3.1(s, 3H); 7.38(d, 1H); 7.89(dd, 1H); 7.98(d, 1H) |
| I.17 | 2-(CH₃—SO₂—)-4-chlorophenyl | C₂H₅ | 0.74(m, 2H); 0.99(m, 2H); 1.18(t, 3H); 2.62(q, 2H); 3.13(s, 3H); 7.13(d, 1H); 7.58(dd, 1H); 7.97(d, 1H) |
| I.18 | 2-Nitro-4-chlorophenyl | C₂H₅ | 0.77(m, 2H); 0.99(m, 2H); 1.18(t, 3H); 2.61(q, 2H); 7.16(d, 2H); 7.66(dd, 1H); 8.2(d, 1H) |
| I.19 | 4-(Phenyl—N=N—)phenyl | C₂H₅ | 0.8(m, 2H); 1.02(m, 2H); 1.21(t, 3H); 2.68(q, 2H); 7.52(m, 3H); 7.63(d, 2H); 7.91(m, 4H) |
| I.20 | 2-Chloro-3-methoxy-4-(CH₃—SO₂—)phenyl | C₂H₅ | 0.78(m, 2H); 0.84(m, 2H); 1.17(q, 2H); 1.46(t, 3H); 2.65(q, 2H); 3.43(q, 2H); 4.26(q, 2H); 7.0(d, 1H); 7.68(d, 1H) |
| I.21 | 2-Chloro-4-nitrophenyl | n-C₃H₇ | 0.77(m, 2H); 0.96(t, 3H); 1.01(m, 2H); 7.32(d, 1H); 8.19(dd, 1H); 8.27(d, 1H) |
| I.22 | 2-Methyl-3-methoxy-4-(CH₃—SO₂—)phenyl | n-C₃H₇ | 0.78(m, 2H); |

TABLE 2-continued

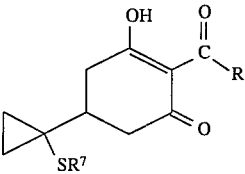

I (A = CH$_2$; R$^2$–R$^6$ = H)

| No. | R$^1$ | R$^7$ | Physical data ($^1$H-NMR: δ[ppm]) |
|---|---|---|---|
| I.23 | 2-(CH$_3$—SO$_2$—)phenyl | n-C$_3$H$_7$ | 0.95(t, 3H); 1.0(m, 2H); 1.57(q, 2H); 2.2(s, 3H); 2.67(t, 2H); 3.22(s, 3H); 3.92(s, 3H); 6.94(d, 1H); 7.83(d, 1H) |
| I.24 | 2-Nitro-4-(CH$_3$—SO$_2$—)phenyl | n-C$_3$H$_7$ | 0.74(m, 2H); 0.95(t, 3H); 1.0(m, 2H); 3.13(s, 3H); 7.18(dd, 1H); 7.63(m, 2H); 8.02(dd, 1H) |
| I.25 | 2-Chloro-4-(CH$_3$—SO$_2$—)phenyl | n-C$_3$H$_7$ | 0.76(m, 2H); 0.94(t, 3H); 1.0(m, 2H); 1.55(q, 2H); 2.56(t, 2H); 3.08(s, 3H); 7.44(d, 1H); 8.26(dd, 1H); 8.77(d, 1H) |
| I.26 | 2-(CH$_3$—SO$_2$—)-4-chlorophenyl | n-C$_3$H$_7$ | 0.76(m, 2H); 0.97(t, 3H); 1.0(m, 2H); 1.58(m, 2H); 2.57(t, 2H); 3.1(d, 3H); 7.38(d, 1H); 7.89(dd, 1H); 7.99(d, 1H) |
| I.27 | 2-Nitro-4-chlorophenyl | n-C$_3$H$_7$ | 0.74(m, 2H); 0.93(t, 3H); 0.97(m, 2H); 2.56(t, 2H); 3.08(s, 3H); 7.12(d, 1H); 7.62(dd, 1H); 7.98(d, 1H) |
| I.28 | 4-(Phenyl—N=N—)phenyl | n-C$_3$H$_7$ | 0.78(m, 2H); 0.95(t, 3H); 0.98(m, 2H); 2.54(t, 2H); 7.18(d, 1H); 7.65(dd, 1H); 8.0(d, 1H) |
| I.29 | 2-Chloro-3-ethoxy-4-(C$_2$H$_5$—SO$_2$—)phenyl | n-C$_3$H$_7$ | 0.63(m, 2H); 0.78(m, 2H); 0.86(t, 3H); 1.42(q, 2H); 7.42(m, 3H); 7.58(m, 2H); 7.68(m, 2H); 7.8(m, 2H) |
|  |  |  | 0.8(m, 2H); 0.92(m, 2H); 0.94(t, 3H); 1.2(t, 3H); 1.44(t, 3H); 1.52(q, 2H); 2.61(t, 2H); 3.43(q, 2H); |

TABLE 2-continued

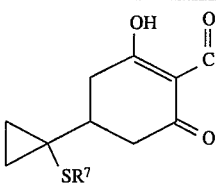

I (A = CH$_2$; R$^2$–R$^6$ = H)

| No. | R$^1$ | R$^7$ | Physical data ($^1$H-NMR: δ[ppm]) |
|---|---|---|---|
| I.30 | 2-Chloro-4-nitrophenyl | Allyl | 4.24(q, 2H); 7.05(d, 1H); 7.76(d, 1H) 0.8(m, 2H); 1.04(m, 2H); 5.18(m, 2H); 5.8(m, 1H); 7.32(d, 1H); 8.19(dd, 1H); 8.25(d, 1H) |
| I.31 | 2-Methyl-3-methoxy-4-(CH$_3$—SO$_2$—)phenyl | Allyl | 0.79(m, 2H); 1.06(m, 2H); 2.2(s, 3H); 3.24(s, 3H); 3.97(s, 3H); 5.1(d, 1H); 5.18(d, 1H); 5.8(m, 1H); 6.97(d, 1H); 7.82(d, 1H) |
| I.32 | 2-(CH$_3$—SO$_2$—)phenyl | Allyl | 0.77(m, 2H); 1.05(m, 2H); 3.1(s, 3H); 5.09(d, 1H); 5.18(d, 1H); 5.8(m, 1H); 7.17(dd, 1H); 7.6(m, 2H); 8.02(dd, 1H) |
| I.33 | 2-Chloro-4-(CH$_3$—SO$_2$—)phenyl | Allyl | 0.78(m, 2H); 1.07(m, 2H); 3.1(s, 3H); 5.09(d, 1H); 5.18(d, 1H); 5.8(m, 1H); 7.38(d, 1H); 7.89(dd, 1H); 7.96(d, 1H) |
| I.34 | 2-Nitro-4-(CH$_3$—SO$_2$—)phenyl | Allyl | 0.79(m, 2H); 1.07(m, 2H); 3.14(s, 3H); 5.08(d, 1H); 5.17(d, 1H); 5.8(m, 1H); 7.44(d, 1H); 8.24(dd, 1H); 8.73(d, 1H) |
| I.35 | 2-(CH$_3$—SO$_2$—)-4-chlorophenyl | Allyl | 0.78(m, 2H); 1.04(m, 2H); 3.13(s, 3H); 5.09(d, 1H); 5.18(d, 1H); 5.8(m, 1H); 7.13(d, 1H); 7.6(dd, 1H); 8.0(d, 1H) |
| I.36 | 2-Nitro-4-chlorophenyl | Allyl | 0.74(m, 2H); 1.04(m, 2H); 5.08(d, 1H); 5.17(d, 1H); 5.8(m, 1H); 7.17(d, 1H); 7.65(dd, 1H); 8.2(d, 1H) |
| I.37 | 4-(Phenyl-N=N—)phenyl | Allyl | 0.8(m, 2H); |

TABLE 2-continued

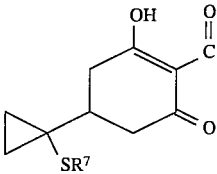

I (A = CH$_2$; R$^2$–R$^6$ = H)

| No. | R$^1$ | R$^7$ | Physical data ($^1$H-NMR: δ[ppm]) |
|---|---|---|---|
| | | | 1.08(m, 2H); 5.08(d, 1H); 5.2(d, 1H); 5.85(m, 1H); 7.5(m, 3H); 7.65(d, 2H); 7.94(m, 4H) |
| I.38 | 2-Chloro-4-nitrophenyl | CH(CH$_3$)$_2$ | 0.8(m, 2H); 1.02(m, 2H); 1.3(dd, 6H); 3.0(m, 1H); 7.34(d, 1H); 8.18(dd, 1H); 8.25(d, 1H) |
| I.39 | 2-Methyl-3-methoxy-4-(CH$_3$—SO$_2$—)phenyl | CH(CH$_3$)$_2$ | 0.78(m, 2H); 1.05(m, 2H); 1.3(dd, 6H); 2.21(s, 3H); 3.25(s, 3H); 3.95(s, 3H); 6.95(d, 1H); 7.84(d, 1H) |
| I.40 | 2-(CH$_3$—SO$_2$—)phenyl | CH(CH$_3$)$_2$ | 0.76(m, 2H); 0.97(m, 2H); 1.26(m, 6H); 3.0(m, 1H); 3.14(s, 3H); 7.18(dd, 1H); 7.6(m, 2H); 7.98(dd, 1H) |
| I.41 | 2-(CH$_3$—SO$_2$—)-4-chlorophenyl | CH(CH$_3$)$_2$ | 0.78(m, 2H); 0.99(m, 2H); 1.24(dd, 6H); 3.02(m, 1H); 3.17(s, 3H); 7.15(d, 1H); 7.6(dd, 1H); 7.98(d, 1H) |
| I.42 | 2-Chloro-3-ethoxy-4-(C$_2$H$_5$—SO$_2$—)phenyl | CH(CH$_3$)$_2$ | 0.78(m, 2H); 1.02(m, 2H); 1.23(m, 9H); 1.46(t, 3H); 3.44(q, 2H); 4.32(q, 2H); 7.06(d, 1H); 7.9(d, 1H) |
| I.43 | 2-Chloro-3-ethoxy-4-(C$_2$H$_5$—SO$_2$—)phenyl | Allyl | 0.76(m, 2H); 1.04(m, 2H); 1.24(t, 3H); 1.48(t, 3H); 3.42(q, 2H); 4.28(q, 2H); 5.07(d, 1H); 5.17(d, 1H); 5.8(m, 1H); 7.05(d, 1H); 7.9(d, 1H) |
| I.44 | 2-(CH$_3$—SO$_2$—)-4-nitrophenyl | n-C$_3$H$_7$ | 0.76(m, 2H); 0.95(t, 3H); 1.0(m, 2H); 1.55(q, 2H); 2.55(t, 2H); 3.15(s, 3H); 7.38(d, 1H); 8.48(dd, 1H); |

TABLE 2-continued

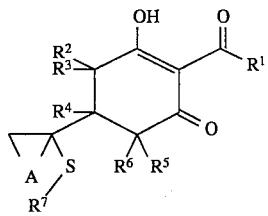

I (A = CH$_2$; R$^2$–R$^6$ = H)

| No. | R$^1$ | R$^7$ | Physical data ($^1$H-NMR: δ[ppm]) |
|---|---|---|---|
| | | | 8.83(d, 1H) |

Use Examples

The herbicidal and growth-regulating action of the 2-aroylcyclohexanediones of the formula I could be demonstrated by greenhouse experiments:

The culture vessels used were plastic flowerpots containing loamy sand with about 3.0% of humus as substrate. The seeds of the test plants were sown separately according to species.

In the preemergence treatment, the active ingredients suspended or emulsified in water were applied directly after sowing, by means of finely distributing nozzles. The vessels were lightly sprinkler-irrigated in order to promote germination and growth and were then covered with transparent plastic covers until the plants began to grow. This covering ensures uniform germination of the test plants, provided that this has not been adversely affected by the active ingredients.

For the postemergence treatment, the test plants were first grown to a height of growth of from 3 to 15 cm, depending on the form of growth, and only thereafter treated with the active ingredients suspended or emulsified in water. For this purpose, the test plants were either sown directly and cultivated in the same vessels or they were first grown separately as seedlings and transplanted into the test vessels a few days before the treatment. The application rate for the postemergence treatment was 3.0 kg/ha of active ingredient.

The plants were kept at 10°–25° C. or 20°–35° C., according to species. The test period extended over 2 to 4 weeks. During this time, the plants were tended and their reaction to the individual treatments was evaluated.

Evaluation was based on a scale from 0 to 100. 100 means no emergence of the plants or complete destruction of at least the above-ground parts and 0 means no damage or normal course of growth.

The growth-regulating action was determined by length measurement. At the end of the experiment, the heights of growth of the treated plants were measured and expressed as a ratio to the height of growth of untreated plants.

The plants used in the greenhouse experiments consisted of the following species:

| Botanical name | Common name |
|---|---|
| *Bromus inermis* | smooth broome |
| *Centaurea cyanus* | cornflower |
| *Echinochloa crus-galli* | barnyard grass |

The result showed that undesirable plants can be very readily controlled with the compounds Nos. 1.4 and 1.5.

We claim:

1. A 2-aroylcyclohexanedione of the formula I where
A is C$_1$–C$_6$-alkylene;
R$^1$ is the phenyl ring or a 5-membered or 6-membered hetaryl ring, each phenyl or hetaryl ring carrying at least one substituent but not more than four substituents, each selected from the group consisting of halogen, cyano, nitro, —N=N—Ph, —S(O)$_m$R$^8$, (C$_1$–C$_4$-alkoxy)carbonyl, —SO$_2$—N(R$^9$)R$^{10}$, —N(R$^9$)—COR$^{10}$, —N(R$^9$)—SO$_2$R$^{11}$, C$_1$–C$_4$-alkyl, C$_1$–C$_4$-alkoxy, C$_1$–C$_4$-haloalkyl and C$_1$–C$_4$-haloalkoxy, where the four last-mentioned radicals are unsubstituted or optionally substituted by one or two of the following: C$_1$–C$_4$-alkoxy, C$_1$–C$_4$-alkylthio and/or cyano, and where two adjacent carbon atoms of the phenyl and hetaryl rings may be bridged by a chain selected from the group consisting of
—C(R$^{12}$)=C(R$^{13}$)—C(R$^{14}$)=C(R$^{15}$)—,
—X—C(R$^{12}$)=N—,
—X—N=C(R$^{12}$)—, —C(R$^{12}$)=N—C(R$^{14}$,R$^{15}$)—X—,
—X—C(R$^{12}$)=N—C(R$^{13}$,R$^{14}$)—,
—X—C(R$^{12}$)=C(R$^{13}$)—,
—X—C(R$^{12}$)=C(R$^{13}$)—C(R$^{14}$,R$^{15}$)—,
—X—C(R$^{12}$,R$^{13}$)—C(R$^{14}$,R$^{15}$)—,
—C(R$^{12}$,R$^{13}$)—X—C($^{14}$,R$^{15}$)—, —X—C(R$^{12}$,R$^{13}$)—Y—,
—X—C(R$^{12}$,R$^{13}$)—C(R$^{14}$,R$^{15}$)—Y—,
—X—C(R$^{12}$,R$^{13}$)—C(R$^{14}$,R$^{15}$)—C(R$^{16}$,R$^{17}$)—,
—C(R$^{12}$,R$^{13}$)—X—C(R$^{14}$,R$^{15}$)—C(R$^{16}$,R$^{17}$)—,
—X—N(R$^{20}$)—X—, —S—N(R$^{20}$)—X—,
—C(R$^{12}$,R$^{13}$)—N(R$^{20}$)—X—, —X—N(R$^{20}$)—Y—N(R$^{21}$)— and
—N(R$^{20}$)—X—N=X(R$^{12}$)—, X and Y independently of one another are each oxygen, sulfur, —SO—, —SO$_2$—, —CO—, —C(R$^{18}$,R$^{19}$)— or —NR$^{20}$— and R$^{12}$ to R$^{19}$ are each hydrogen, halogen, hydroxyl, C$_1$–C$_4$-alkyl, C$_1$–C$_4$-alkoxy, C$_1$–C$_4$-alkylthio, C$_1$–C$_4$-alkylamino, di-(C$_1$–C$_4$-alkyl)amino or phenyl and R$^{20}$ and R$^{21}$ are each hydrogen, C$_1$–C$_4$-alkyl, C$_1$–C$_4$-alkoxy, (C$_1$–C$_4$-alkyl)carbonyl, phenyl or benzoyl;

Ph is phenyl which is unsubstituted or optionally is substituted by from one to three substituents selected from the group consisting of halogen, cyano, nitro, $-S(O)_nR^{22}$, $(C_1-C_4\text{-alkoxy})\text{carbonyl}$, $-SO_2-N(R^{23})R^{24}$, $-N(R^{23})-COR^{24}$, $-N(R^{23})-SO_2R^{25}$, $C_1-C_4$-alkyl, $C_1-C_4$-alkoxy, $C_1-C_4$-haloalkyl and $C_1-C_4$-haloalkoxy, where the four last-mentioned radicals in turn optionally are substituted by one or two of the following substituents: $C_1-C_4$-alkoxy, $C_1-C_4$-alkylthio and/or cyano;

m and n are each 0, 1 or 2;

$R^8$ and $R^{22}$ independently of one another are each $C_1-C_4$-alkyl or $C_1-C_4$-haloalkyl, where these groups are unsubstituted or, are substituted by one or two $C_1-C_4$-alkoxy, $C_1-C_4$-alkylthio and/or cyano radicals;

$R^9$, $R^{10}$, $R^{23}$ and $R^{24}$ independently of one another are each hydrogen, $C_1-C_4$alkyl, $C_1-C_4$-haloalkyl, unsubstituted phenyl or phenyl which carries from one to three radicals selected from the group consisting of halogen, $C_1-C_4$-alkyl and $C_1-C_4$-alkoxy;

$R^{11}$ and $R^{25}$ independently of one another are each $C_1-C_4$-alkyl or $C_1-C_4$-haloalkyl, where these groups optionally carry one or two cyano, phenyl and/or benzyl radicals;

$R^2$, $R^3$, $R^4$ and $R^5$ independently of one another are each hydrogen or $C_1-C_4$-alkyl;

$R^6$ is hydrogen, $C_1-C_4$-alkyl or $(C_1-C_4\text{-alkoxy})$-carbonyl;

$R^7$ is $C_1-C_4$-alkyl, with the proviso that $R^1$ is not mono- or dihalophenyl, or the agriculturally useful salts thereof or the esters of I with $C_1-C_{10}$-carboxylic acids or inorganic acids.

2. A 2-aroylcyclohexanedione of the formula I as defined in claim 1, wherein at least one substituent on the phenyl or hetaryl ring $R^1$ is $-N=N-Ph$, $-S(O)_mR^8$, $(C_1-C_4\text{-alkoxy})\text{carbonyl}$, $-N(R^9)-SO_2R^{11}$, $-SO_2NR^9R^{10}$, $-N(R^9)-COR^{10}$ or $C_1-C_4$-haloalkyl.

3. A herbicidal composition a herbicidal amount of at least one 2-aroylcyclohexanedione of the formula I or an agriculturally useful salt or an ester of I, as defined in claim 1, and at least one inert liquid or solid carrier and, optionally, at least one adjuvant.

4. A method for controlling undesirable plant growth, wherein a herbicidal amount of at least one 2-aroylcyclohexanedione of the formula I or an agriculturally useful salt or an ester of I, as defined in claim 1, is caused to act on plants or their habitat or on seed.

5. A plant growth regulator containing inert carriers and an amount, sufficient for regulating plant growth, of at least one 2-aroylcyclohexanedione of the formula I or of a salt or ester of I, as defined in claim 1.

6. A method for regulating plant growth, wherein an amount, sufficient for regulating plant growth, of at least one 2-aroylcyclohexanedione of the formula I or of an agriculturally useful salt or ester of I, as defined in claim 1, is allowed to act on plants or their habitat or on the seed of the plants.

* * * * *

UNITED STATES PATENT AND TRADEMARK OFFICE
CERTIFICATE OF CORRECTION

PATENT NO.: 5,559,218

DATED: September 24, 1996

INVENTOR(S): KAST et al.

It is certified that error appears in the above-identified patent and that said Letters Patent is hereby corrected as shown below:

Column 39, claim 1, line 6, "$C_1-C_4$-alkyl" should read --$C_1$-$C_4$-alkyl--.

Column 39, claim 1, line 6, "$C_1-C_4$-haloalkyl" should read --$C_1$-$C_4$-haloalkyl--.

Column 39, claim 1, line 7, "$C_1-C_4$-haloalkoxy" should read --$C_1$-$C_4$-haloalkoxy--.

Column 39, claim 1, line 18, "$C_1$-$C_4$alkyl" should read --$C_1$-$C_4$-alkyl--.

Column 40, claim 3, line 8, "composition a" should read
    --composition containing a--.

Signed and Sealed this

Fourteenth Day of January, 1997

Attest:

BRUCE LEHMAN

Attesting Officer

Commissioner of Patents and Trademarks